US008540967B2

(12) United States Patent
Barrett et al.

(10) Patent No.: US 8,540,967 B2
(45) Date of Patent: Sep. 24, 2013

(54) PORPHYRAZINE OPTICAL AND DUAL OPTICAL/MR CONTRAST AND THERAPEUTIC AGENTS

(75) Inventors: Anthony G. M. Barrett, London (GB); Evan R. Trivedi, Evanston, IL (US); Brian M. Hoffman, Evanston, IL (US)

(73) Assignee: Hoffman/Barrett, L.L.C., Evanston, IL (US)

( * ) Notice: Subject to any disclaimer, the term of this patent is extended or adjusted under 35 U.S.C. 154(b) by 180 days.

(21) Appl. No.: 13/062,031

(22) PCT Filed: Sep. 4, 2009

(86) PCT No.: PCT/US2009/055991
§ 371 (c)(1), (2), (4) Date: Jul. 29, 2011

(87) PCT Pub. No.: WO2010/028216
PCT Pub. Date: Mar. 11, 2010

(65) Prior Publication Data
US 2011/0293531 A1    Dec. 1, 2011

Related U.S. Application Data

(60) Provisional application No. 61/095,026, filed on Sep. 8, 2008.

(51) Int. Cl.
*A61B 5/055* (2006.01)

(52) U.S. Cl.
USPC ........ 424/9.362; 424/1.69; 424/9.1; 424/9.61

(58) Field of Classification Search
USPC ................. 424/9.1, 9.3, 9.362, 9.6; 540/121, 540/128, 131, 132, 135, 139, 140, 145
See application file for complete search history.

(56) References Cited

FOREIGN PATENT DOCUMENTS
WO    WO-2004101516 A2    11/2004

OTHER PUBLICATIONS

Neal D. Hammer et al. Charge Dependence of Cellular Uptake and Selective Anittumor Activity of Porpyrazines, J. Med. Chem. 2005, 48, 8125-8133.*
Morgan, A., et al., "Synthesis and Photodynamic Activity of Some Tetraazoporphrin Derivatives," *European Journal of Medicinal Chemistry*, vol. 32, No. 1 (Jan. 1, 1997), pp. 21-26.
Lee, et al., "Tuning the Singlet Oxygen Quantum Yield of Near-IR-Absorbing Porphyrazines," *Photochemistry and Photobiology*, 2003, vol. 77(1), pp. 18-21.
Hammer, N., et al., "Charge Dependence of Cellular Uptake and Selective Antitumor Activity of Porphyrazines," *European Journal of Medicinal Chemistry*, LNK-PUBMED: 16366594, vol. 48, (Dec. 11, 2005), pp. 8125-8133.
Vesper, B., et al., "Developing a Structure-Function Relationship for Anionic Porphyrazines Exhibiting Selective Anti-Tumor Activity," *Journal of Photochemistry and Photobiology B*: Biology 82 (2006), pp. 180-186.
Lee, S., et al., "Synthesis and Biological Analysis of Thiotetra(ethylene glycol) monomethyl Ether-Functionalized Porphyrazines: Cellular Uptake and Toxicity Studies," *Metal-Based Drugs* 2008 LNKD-PUBMED: 18274661, vol. 2008, pp. 1-13.
Sholto, A., et al., "Spectroscopy, Binding to Liposomes and Production of Singlet Oxygen by Porphyrazines with Modularly Variable Water Solubility," *Photochemistry and Photobiology*, vol. 84 (2008), pp. 764-773.
Fuchter, Matthew, et al., "Porphyrazines: Designer Macrocycles by Peripheral Substitute Change," *Australian Journal of Chemistry*, vol. 61, No. 4 (Apr. 24, 2008), pp. 235-255.
Trivedi, E., et al., "NIR Tumor Contrast Agents Based on Porphyrazines: Synthesis and in Vitro Cellular Uptake," 1996-2010, presentation No. 1642, OASIS [online], Sep. 13, 2008 [retrieved on Jun. 25, 2010]. Retrieved from the Internet: <URL:http://www.abstractsonline.com/viewer/viewAbstractasp?CKey={B6E18C19-F488-4990-AB15-C8238409C100}&MKey={B47BAE74-CCA9-4C27-80FB-0005AFC9E5C0}&AKey={A4C6DD8F-4BF2-400D-97ED-20C14381CDBB}&SKey={E203CEC3-9D18-446E-A056-23232B15ABF9}>>.
Harney, A., et al., "NIR Tumor Contrast Agents Based on Porphyrazines: Tumor-Selective Retention in Vivo," presentation No. 1623, OASIS [online], Sep. 13, 2008 [retrieved on Jun. 25, 2010]. Retrieved from the Internet: <URL:http://www.abstractsonline.com/viewer/viewAbstract.asp?CKey={EED3B68A-7A59-4CD3-BC79-3A531BBB321B}&MKey={B47BAE74-CCA9-4C27-80FB-0005AFC9E5C0}&AKey={A4C6DD8F-4BF2-400D-97ED-20C14381CDBB}&SKey={E203CEC3-9D18-446E-A056-23232B15ABF9}>>.
International Search Report in PCT Application No. PCT/US2009/055991, dated Nov. 17, 2011.

* cited by examiner

*Primary Examiner* — Michael G Hartley
*Assistant Examiner* — Jagadishwar Samala
(74) *Attorney, Agent, or Firm* — Marshall, Gerstein & Borun LLP

(57) ABSTRACT

Porphyrazines capable of localizing in a tumor of a mammal are disclosed. The porphyrazines are used in methods of imaging a tumor and in methods of treating tumors, either alone or in combination with a chemotherapeutic agent and/or radiation.

21 Claims, 4 Drawing Sheets

US 8,540,967 B2

PORPHYRAZINE OPTICAL AND DUAL OPTICAL/MR CONTRAST AND THERAPEUTIC AGENTS

CROSS REFERENCE TO RELATED APPLICATIONS

This application is the U.S. National Phase application of PCT/US2009/055991, filed Sept. 4, 2009, which claims the benefit of U.S. provisional patent application No. 61/095,026, filed Sep. 8, 2008, incorporated by reference herein in its entirety.

STATEMENT OF GOVERNMENTAL INTEREST

This invention was made with government support under Grant Number CHE0500796 awarded by the National Science Foundation. The government has certain rights in the invention.

FIELD OF THE INVENTION

The present invention relates to porphyrazine compounds, and the use of the porphyrazine compounds in the imaging and treatment of tumors. The porphyrazines are capable of localizing in a tumor, and permit detection of the tumor by visualization techniques, such as optical imaging and magnetic resonance (MR) imaging. The porphyrazines also reduce the size of, or eliminate, tumors either when administered alone (with or without light activation), or in conjunction with a chemotherapeutic agent or radiation including visible and near infrared light, or when conjugated to a chemotherapeutic agent different from a porphyrazine.

BACKGROUND OF THE INVENTION

Survival rates of breast cancer patients could be improved if tumors are detected in their early stages or, following treatment such as chemotherapy, surgery, or radiation, residual cancer cells easily can be detected at the cellular level. The primary technique for early screening for breast cancer, i.e., x-ray mammography, is effective, but has disadvantages. The differentiation between normal tissue and cancerous tissue based on their relative density is small, causing false-positives and subjecting patients to additional testing that may be unnecessary, invasive, and often painful. Furthermore, exposure to ionizing radiation inherent to x-ray procedures limits the frequency that high-risk patients can be screened. The limited sensitivity of this technique allows small, early-stage tumors to be missed, as well as the failure to recognize residual cancer cell clusters after treatment thereby permitting the disease to progress between screenings. Implementation of new, sensitive, and safe detection methods would improve the diagnosis of breast cancer and prognosis of breast cancer patients by reducing levels of morbidity and mortality.

Fluorescence imaging using near-infrared (NIR) contrast agents is an emerging, highly sensitive method for tumor detection that takes advantage of the relative transparency of mammalian tissue to NIR light (about 700-1000 nm). A contrast agent that absorbs and emits light in the visible and NIR and accumulates specifically in tumor tissue could be optically imaged through soft tissue, thereby providing an ideal, non-invasive detection method for superficial tumors in soft tissue, such as those of the breast.

Optical absorbance/fluorescence or phosphorescence imaging of soft tissue with light at visible and near-infrared (NIR) wavelengths within the window of relative tissue transparency therefore represents an important emerging method of tumor detection, but, as with other imaging modalities, effective optical contrast agents are needed. Porphyrazines (pzs), a class of porphyrinoid macrocycles, exhibit a combination of photophysical, chemical, and biological properties that make them uniquely attractive both as optical tumor-imaging agents and as a platform for dual-mode optical/magnetic resonance (MR) imaging agents.

SUMMARY OF THE INVENTION

The present invention is directed to porphyrazine compounds and use of the porphyrazines compounds in imaging and detecting tumors in a mammal, and in the size reduction and elimination of such tumors.

Visible and near infrared (NIR) optical imaging is emerging as a precise, non-invasive means for breast cancer diagnosis and the diagnosis of other cancers in soft tissue, including skin and testicular cancers. Tumor-specific fluorescent contrast agents, such as the chiral porphyrazine compounds of the present invention, greatly improve early stage and post remedial intervention cancer detection. Therefore, one aspect of the present invention is to provide porphyrazine compounds capable of localizing in a tumor. The present porphyrazine compounds fluoresce within the visible or NIR wavelength range (e.g., about 730 nm), demonstrate tumor-cell uptake in vitro, and also exhibit tumor-specific accumulation and retention in subcutaneous tumors in vivo, where a strong fluorescence is displayed with a negligible background.

The present invention includes embodiments in which (a) the porphyrazine acts as a visual or NIR optical imaging agent to detect tumors, (b) the porphyrazine exhibits a toxicity with respect to tumor cells and therefore can reduce the size of, or eliminate, the tumor, either when administered alone (with or without light activation) or in conjunction with another cancer treatment modality, i.e., chemotherapy, radiation, and/or surgery, (c) the porphyrazine can be linked to an MR imaging agent, such as a gadolinium complex, to provide a conjugate that localizes in a tumor and permits a dual optical/MR detection of the tumor with an attendant improvement in the three dimensional quality of the image, and (d) the porphyrazine can be linked to a non-pz chemotherapeutic agent, such as aromasin, tamoxifen, taxotere, xeloda, methotrexate, doxorubicin, to provide a conjugate that localizes in a tumor to enhance the efficacy of the chemotherapeutic agent as well as providing a real-time, non-invasive imaging of the therapeutic agent in the patient during treatment.

Therefore, another aspect of the present invention is to provide a method of detecting a tumor in a mammal by administering a sufficient amount of a porphyrazine compound of the present invention for visualization to an individual, then visualizing the porphyrazine in the mammal. The visualizing can be one or more of optical imaging, NIR imaging, PET imaging, MR imaging, and similar imaging techniques. In this aspect of the invention, two or more imaging methods can be used after the administration of a single porphyrazine compound of the present invention.

Still another aspect of the present invention is to provide a method of treating an individual having a tumor, wherein a porphyrazine compound is administered to the individual in a sufficient amount to localize in the tumor and kill tumor cells, with or without light activation. In yet another aspect, a porphyrazine compound is linked to a non-pz chemotherapeutic agent, and the resulting conjugate is administered to an individual having a tumor in order to reduce the size of, or eliminate, the tumor while providing real-time, non-invasive imaging of the tumor and it reduction during therapy.

In other aspects, embodiments of the present invention further provide kits and methods of use in imaging for research, diagnostic, and clinical applications.

These and other novel aspects of the present invention will become apparent from the following detailed description of the preferred embodiments.

DETAILED DESCRIPTION OF THE PREFERRED EMBODIMENTS

Figure 1:
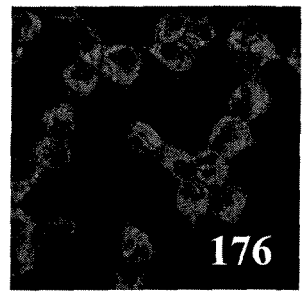
FIG. 1 is a confocal image of NIR fluorescence of compound 176 in A549 lung carcinoma cells (magnification, 63×)

The present invention is directed to porphyrazines (pzs) that exhibit a combination of optical, chemical, and biological properties making them uniquely attractive both as optical absorbance/fluorescence tumor-imaging agents and as a platform for multi-modal optical/MRI imaging agents. Test results showed that the present pz compounds exhibit intense optical absorbance and fluorescence in the NIR window with optimum tissue penetration, and are selectively taken up by tumor cells and by tumors in vivo. In addition, their flexible mode of synthesis permits coupling of the pzs with non-pz chemotherapeutic agents and MR relaxivity agents to form a conjugate. As used herein, "pz conjugate" means a pz linked with a MR imaging agent or a non-pz chemotherapeutic agent.

The present pzs also are capable of reducing the size of and/or eliminating tumors, either alone (with or without light activation) or in combination with other tumor treatment modalities, such as surgery, chemotherapy, and/or radiation. The present pzs further can be linked to a non-pz chemotherapeutic agent in order to provide a conjugate that localizes the chemotherapeutic agent in the tumor and thereby enhance control of the tumor and the direct, non-invasive visualization of the reduction in tumor volume during therapy.

The present invention therefore relates to heteroatom-functionalized pzs and their use as optical and dual-mode optical/MR imaging agents, the dual mode agents being generated by linking paramagnetic contrast agents to the heteroatom-functionalized pzs. Embodiments of the present invention include the use of such conjugates as optical/dual MR imaging therapeutic agents. The present pzs also are useful chemotherapeutic agents per se, and further can be linked to non-pz chemotherapeutic agents provide a pz-chemotherapeutic conjugate that targets and localizes the chemotherapeutic agent in a tumor.

Studies of sulfur-functionalized pzs support their potential use as optical imaging agents (1-4). It now has been discovered that oxygen-functionalized pzs exhibit highly selective in vivo tumor uptake and enable precise fluorescence imaging. Further, dual-mode optical/MR imaging agents that exhibit high MR relaxivity in addition to NIR luminescence have been synthesized.

Heteroatom-functionalized porphyrazines (pzs) and their derivatives are porphyrinoid macrocycles that have recently been considered as optical contrast agents for tumor detection and as a platform for cancer treatment using photodynamic therapy (PDT). These pzs have intense NIR absorption/emission and are synthetically flexible, making it possible to design a pz having desirable NIR optical characteristics, while independently adjusting amphiphilicity and cell recognition, properties that dictate tumor-specific retention of the porphyrazines.

Porphyrazines (pzs) are aromatic macrocycles different from porphyrins in that the meso carbons are replaced with nitrogen. The meso-nitrogen atoms confer intense NIR absorption and emission, thereby making pzs excellent photosensitizers for the detection of superficial cancers via optical imaging. Compounds of the present invention therefore have the following macrocyclic core, abbreviated herein as "pz":

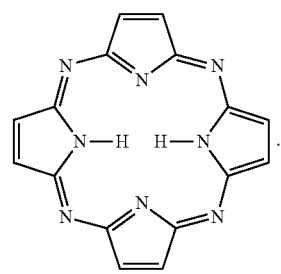 [SMILES: C1=Cc2nc1nc1ccc(nc3nc(nc4ccc(n2)[nH]4)C=C3)[nH]1]

Porphyrazine compounds of the present invention have a general structure:

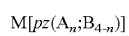

wherein pz is defined above;

M is 2H or a metal ion capable of complexing with pyrrole nitrogen atoms;

n is 1-3;

A is $(-N(R^1)_2)_2$, $(-OR^1)_2$, or $(-SR^1)_2$;

B is a benzo ring fused on the pz, substituted with one or more $-XR^2$ group, wherein X is O or S;

$R^1$, independently, and $R^2$, independently, are selected from the group consisting of $C_{1-6}$alkyl optionally substituted with OH, $OR^3$, $N(R^3)_2$, $CO_2R^3$, or $CON(R^3)_2$, $C_{3-6}$cycloalkyl optionally substituted with OH, $OR^3$, $N(R^3)_2$, $CO_2R^3$, or $CON(R^3)_2$, $(CH_2)_{1-3}C_{3-6}$cycloalkyl optionally substituted with OH, $OR^3$, $N(R^3)_2$, $CO_2R^3$, or $CON(R^3)_2$, $(CH_2)_{1-6}C_6H_5$ optionally substituted with OH, $OR^3$, $N(R^3)_2$, $CO_2R^3$, or $CON(R^3)_2$, wherein each $R^3$ independently is H, $C_{1-6}$alkyl, $C_{3-6}$cycloalkyl, or $(CH_2)_{1-3}C_{3-6}$cycloalkyl;

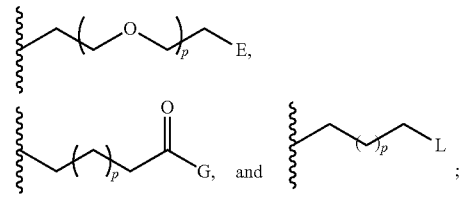

p is 0-10; wherein

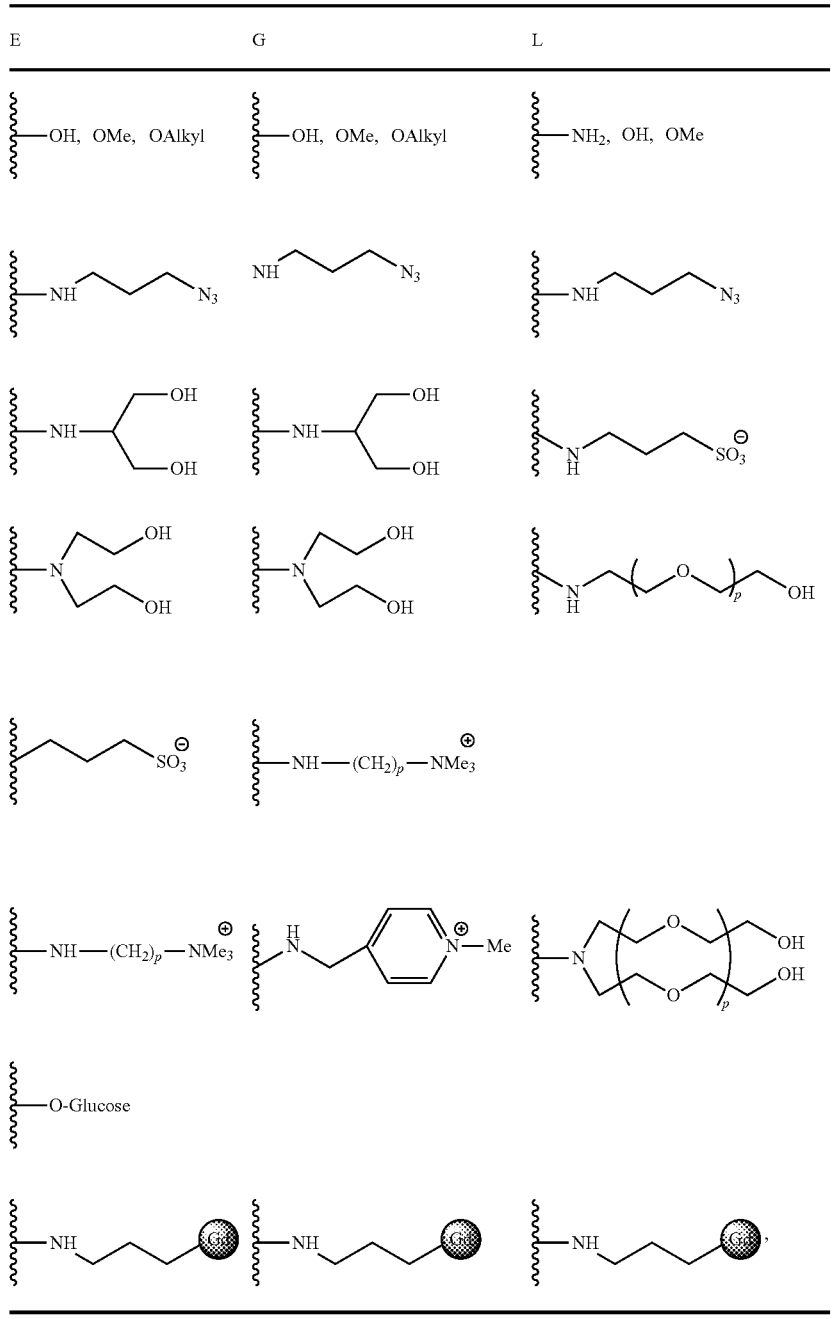

and

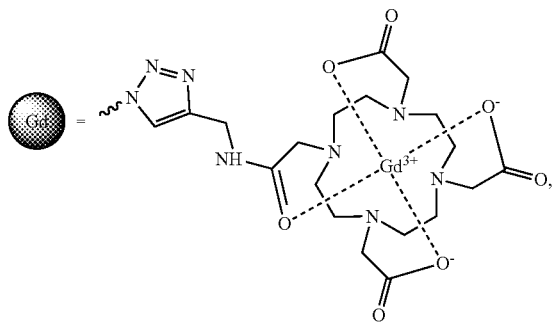

or two R' groups can be taken together to form a 5- or 6-membered ring.

For example, two $R^1$ groups can be taken together (R—R) as shown in below, or their antipodes:

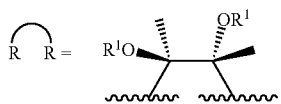

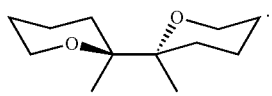

As used herein, the term "alkyl" refers to linear and branched alkyl groups, including, but not limited to, methyl, ethyl, n-propyl, isopropyl, n-butyl, tert-butyl, and 3-methyl-2-butyl.

As used herein, "M" in the porphyrazine is 2H or any metalloid or metal ion capable of complexing with the pyrrole nitrogen atoms of the porphyrazine. "M" of porphyrazine compounds therefore can be two hydrogen atoms or a metal ion, including but are limited to, alkali metals, alkaline earth metals, transition metals or all three periods. lanthanides, and actinides. Nonlimiting examples of "M" include nickel, copper, two hydrogen atoms, magnesium, iron, aluminum, manganese, gadolinium, rhodium, indium, thallium, lutetium, gold, cobalt, titanium, lead, platinum, palladium, ruthenium, lithium, zinc, ytterbium, neodymium, chromium, technetium, silicon, germanium, tin, molybdenum, zirconium, tungsten, rhenium, iridium, uranium, thorium, gallium, and vanadium. The identity of a particular "M" depends upon the physical and chemical properties desired in porphyrazine compound. In some preferred embodiments, "M" is 2H, Mg, Zn, Cu, or Mn.

The present pz compounds are prepared by the condensation of maleonitrile/isoindoline derivatives, and therefore offer chemical flexibility with appended sulfur, oxygen, or nitrogen heteroatoms directly attached to and coupled with the pz aromatic core. Synthetic routes to the present $M[pz(A_n; B_{4-n})]$ pzs allow the independent optimization of their tumor delivery and photophysical characteristics and, in some cases, intrinsic toxicity to tumor cells. Preferred pzs of the invention have a structure $M[pz(A_2; B_2)]$, and more preferred are the $M[pz(trans-A_2; B_2]$ compounds.

The M[pz(trans-A2; B2)] compounds exhibit excellent optical properties and an extensive library of such pzs has been prepared. Cellular uptake monitored by confocal fluorescence microscopy is dependent on the pz's overall amphiphilicity, and qualitative analysis indicates preferential uptake into tumor cells (e.g., A549) over non-tumorigenic cells (e.g., WI38 VA13).

The following synthetic scheme illustrates the synthesis of compound 247 and related chiral O- and S-appended pzs. In particular, (5R,6R)2,3-dicyano-5,6-dimethoxy-5,6-dimethyldiox-2-ene (1) and 4,7-bis(isopropyloxy)-1,3-diiminoisoindoline (2) were prepared by literature procedures and subjected to magnesium templated cyclization conditions to yield pzs 241-257 (Scheme A). The method used to synthesize a related chiral sulfur appended porphyrazine 300-cR is shown in Scheme B.

Scheme A

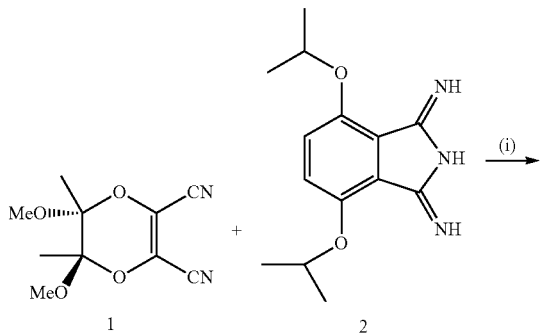

-continued
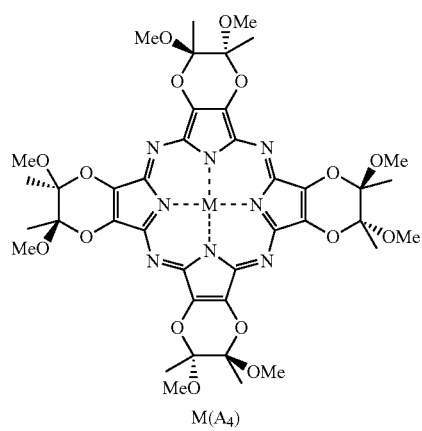
M(A₄)
(ii) ⎰ 242 M = Mg
     ⎱ 241 M = H₂
(iii) → 243 M = Zn
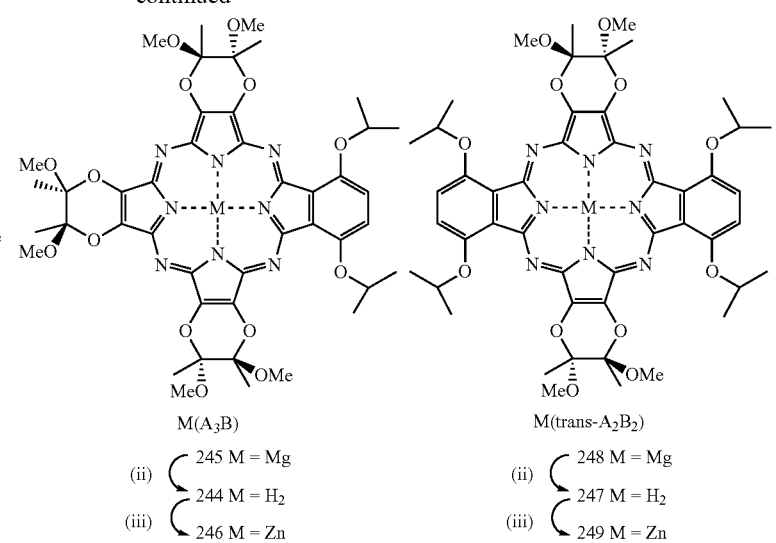
M(A₃B)
(ii) ⎰ 245 M = Mg
     ⎱ 244 M = H₂
(iii) → 246 M = Zn
M(trans-A₂B₂)
(ii) ⎰ 248 M = Mg
     ⎱ 247 M = H₂
(iii) → 249 M = Zn
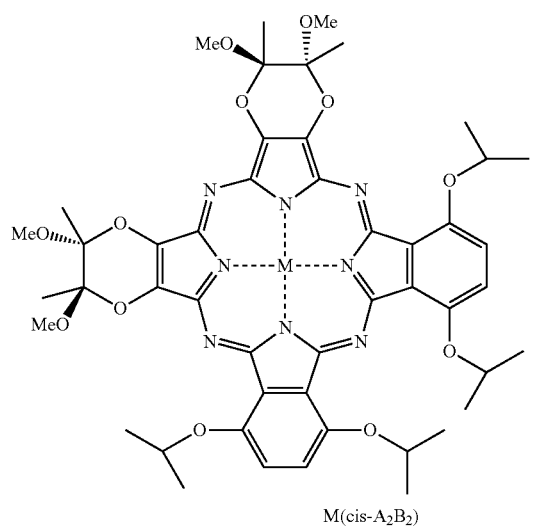
M(cis-A₂B₂)
(ii) ⎰ 258 M = Mg
     ⎱ 254 M = H₂
(iii) → 255 M = Zn
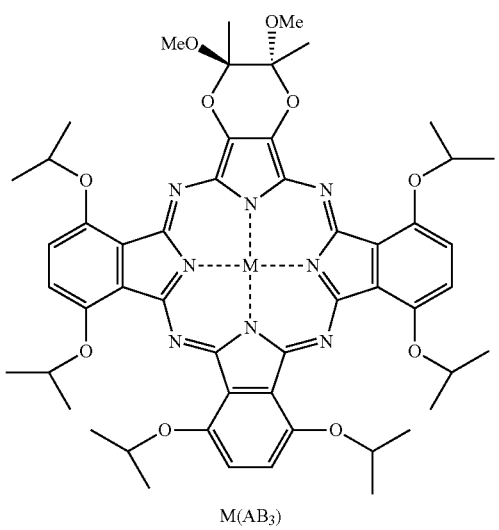
M(AB₃)
(ii) ⎰ 259 M = Mg
     ⎱ 256 M = H₂
(iii) → 257 M = Zn
(i) Mg(OPr)₂, n-PrOH, reflux 18hrs; (ii) acetic acid, CH₂Cl₂, 24hrs; (iii) Zn(OAc)₂, MeOH, 24hrs

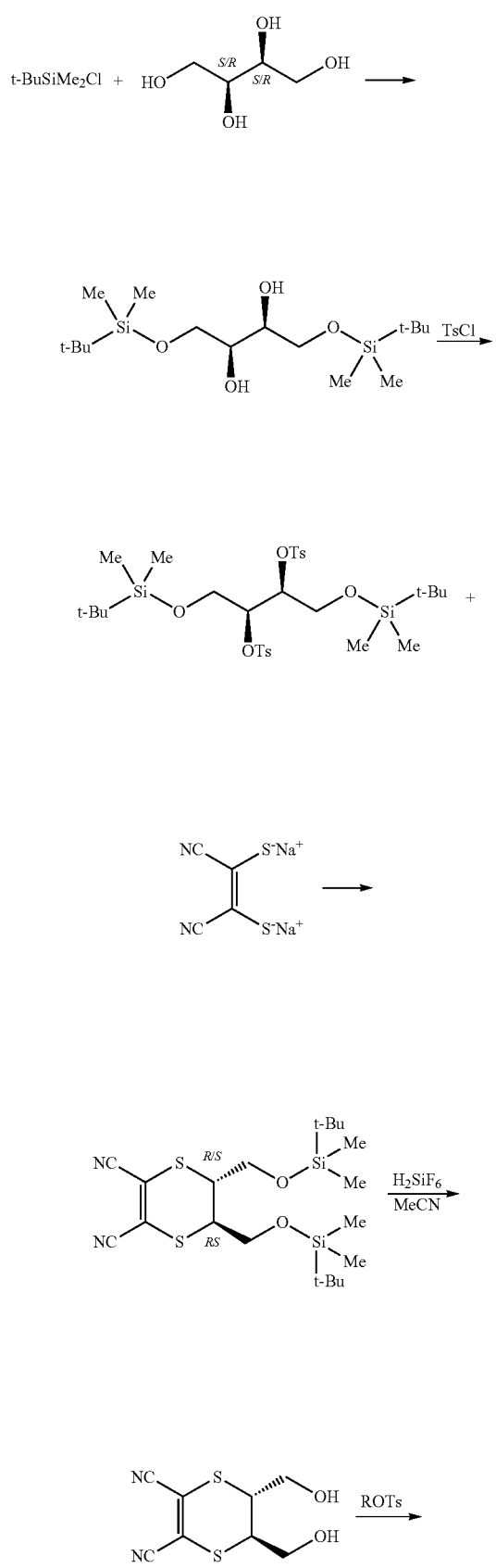

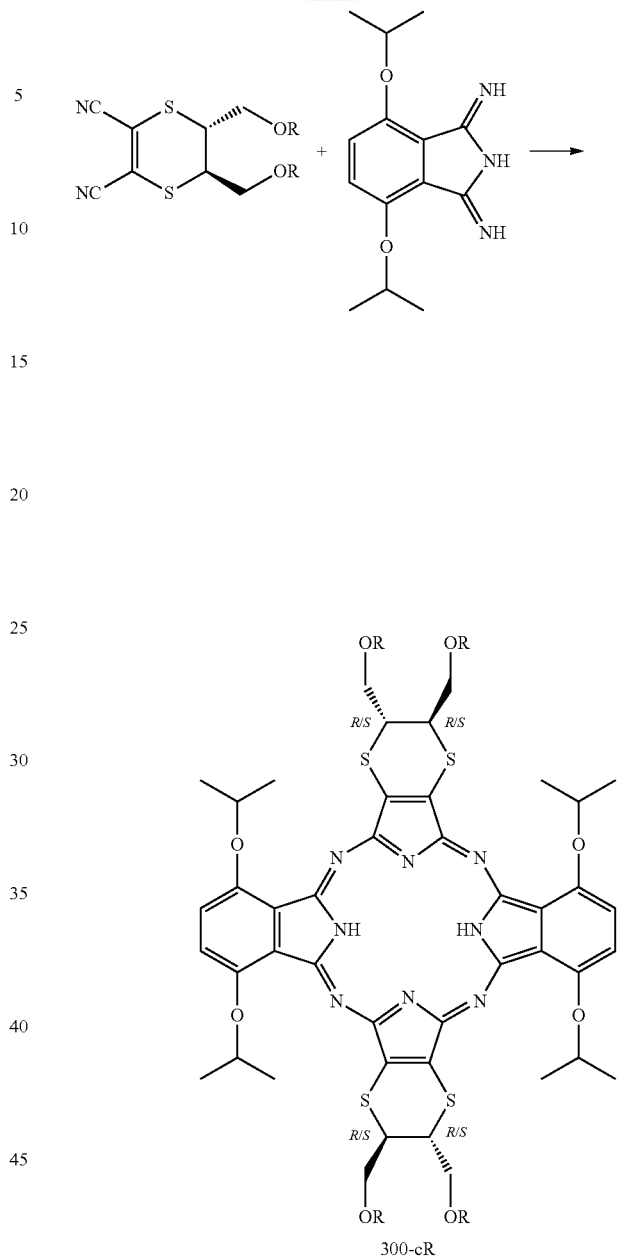

300-cR

The following synthetic schemes show a general procedure for the synthesis of multi-modal pz-Gd (i.e., $Gd^{3+}$-appended) conjugates. These conjugates allow both NIR and MR imaging of a tumor. Free-base pz-azides were synthesized from the $A_2B_2$-4 ester by complete and sub-stoichiometric hydrolysis followed by a NHS ester coupling using 1-azido-3-aminopropane or bis(2-azidoethyl) amine as nucleophiles (Scheme C). Metallation of free-base pz-azides with $ZnCl_2$ yielded the Zn-pz-azides in quantitative yield. Click chemistry was employed to couple these Zn-pz-azides with $Gd^{3+}$ DOTA-alkyne chelates. Application to the metal-free pz yields the Cu-pz (for example, Scheme D). The final conjugates possess 1, 2, 4, and 8 appended $Gd^{3+}$ chelates.

Scheme C
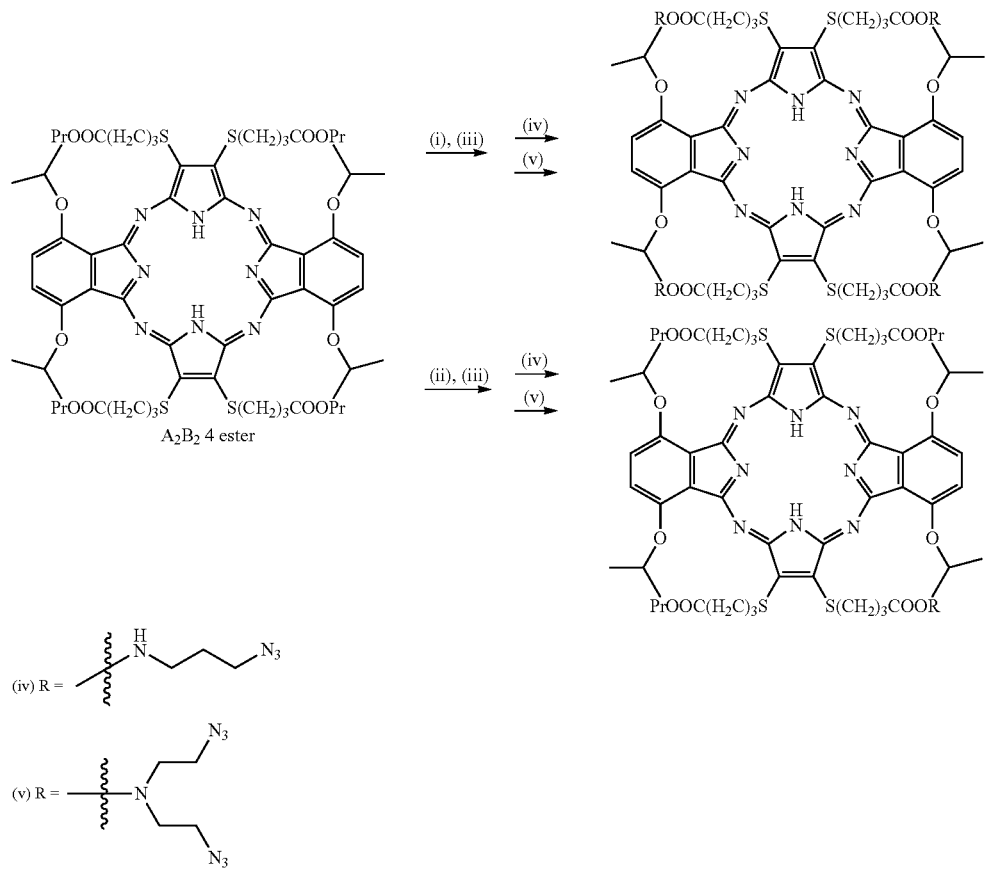
(i) 4 eq LiOH, THF/H₂O; (ii) 1 eq LiOH, THF/H₂O; (iii) DCC/NHS (dicyclocarbodiimide/N-hydroxysuccinimide), THF;
(iv) 1-azido-3-aminopropane, CH₂Cl₂; (v) bis(2-azidoethyl)amine, CH₂Cl₂
Scheme D
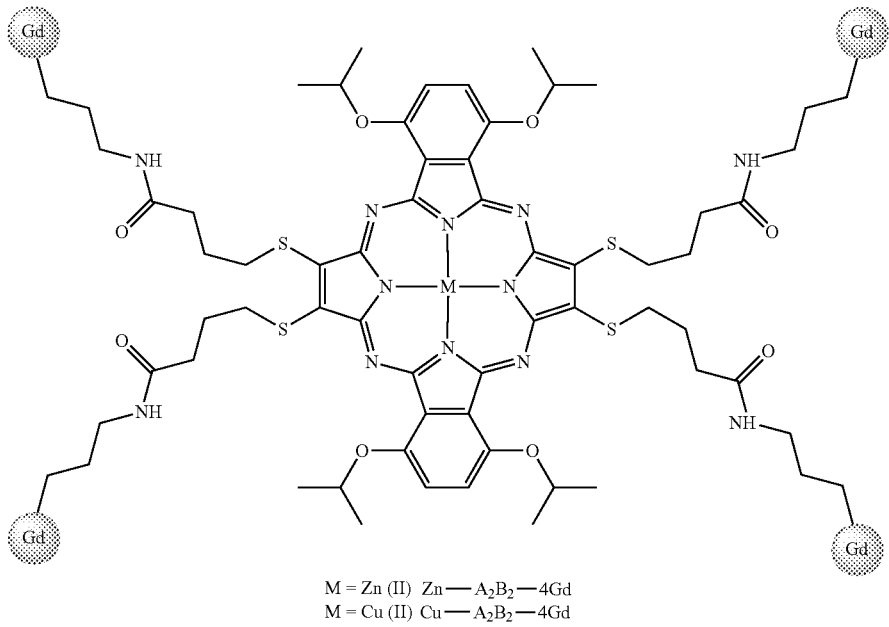
M = Zn (II)   Zn—A₂B₂—4Gd
M = Cu (II)   Cu—A₂B₂—4Gd -continued
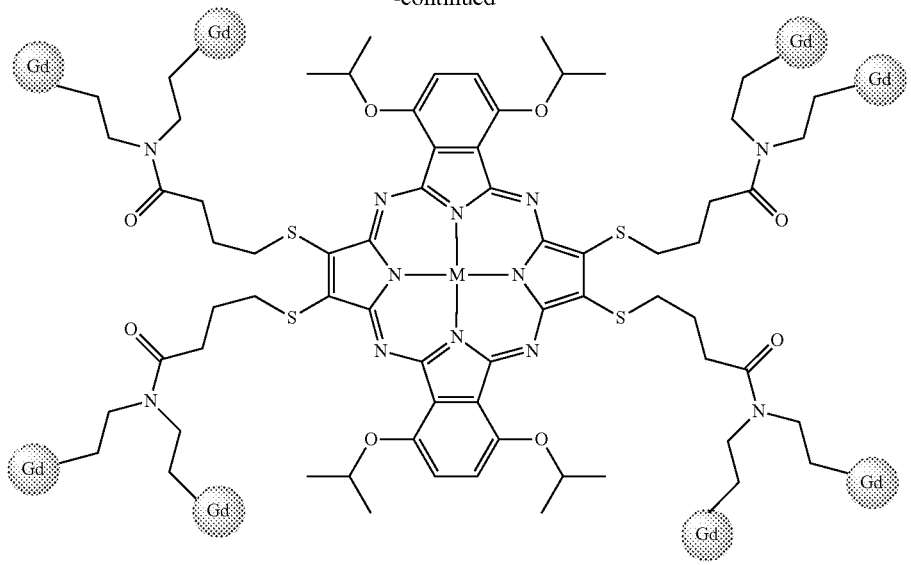
M = Zn (II)  Zn—A$_2$B$_2$—8Gd
M = Cu (II)  Cu—A$_2$B$_2$—8Gd
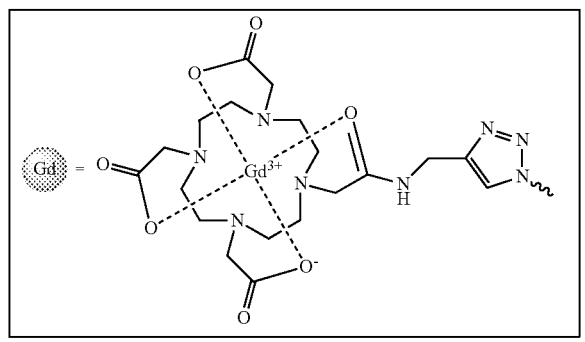
The following compound exemplifies a dual imaging compound of the present invention containing eight gadolinium complexes (Gd). A present pz compound can contain one to eight Gd complexes, as desired or needed. In the Gd8-Mpz compound below, M is 2H, Mg, Zn, or Cu, and preferably is Zn or Cu.
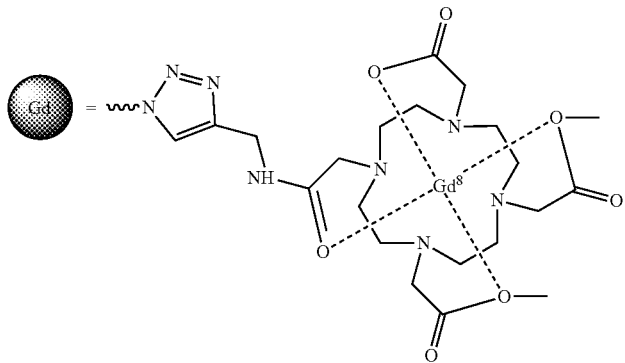

-continued
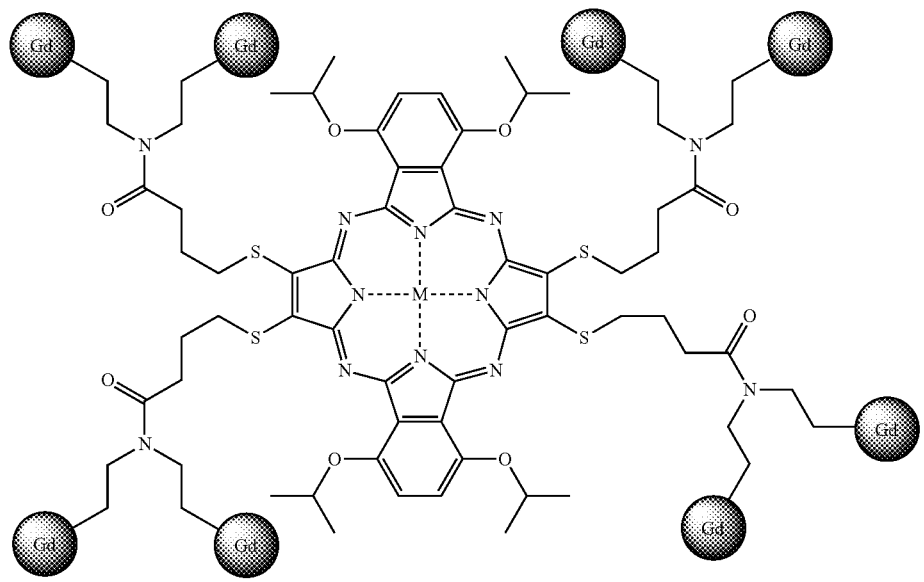
Gd8-pz
The following are specific pz compounds capable of localizing in tumors to enhance imaging and/or to kill tumor cells.
Compound 176
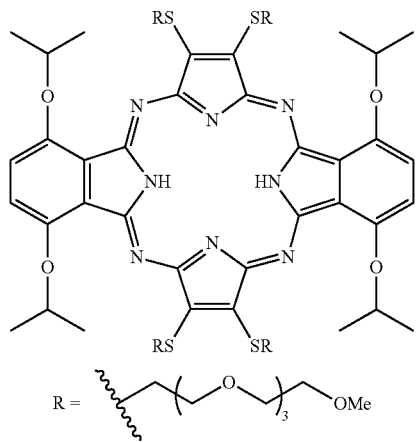
Compound 247
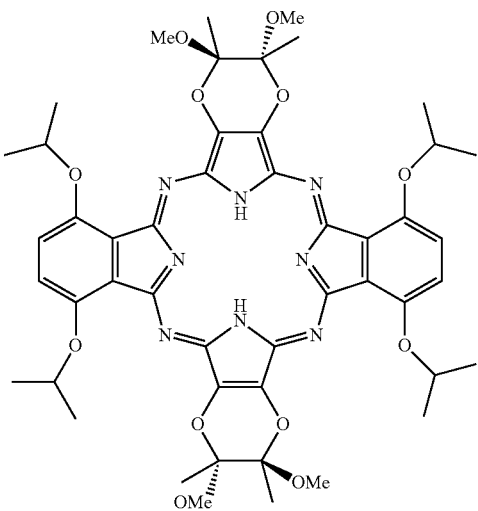

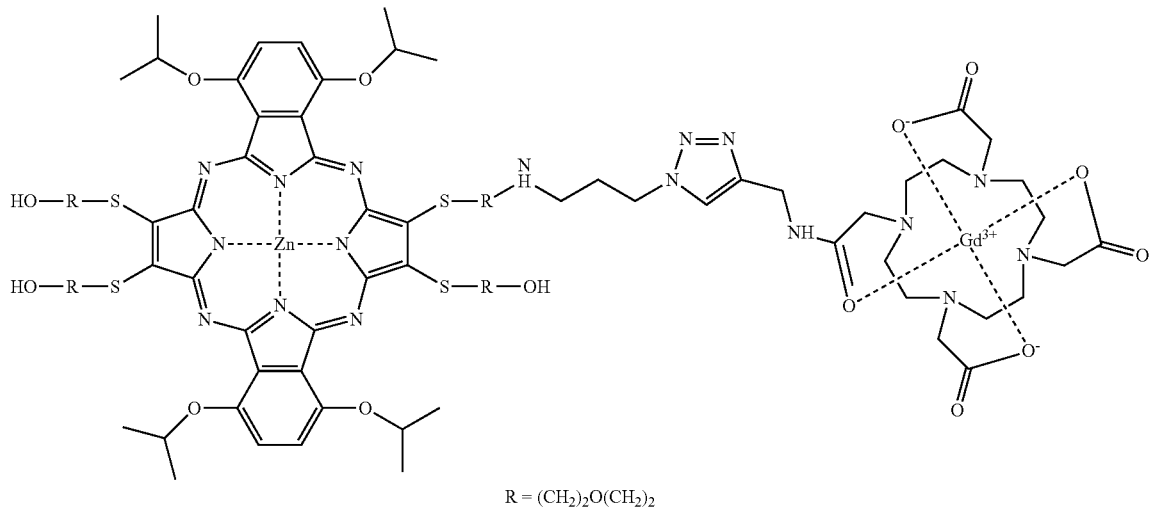

Compound 270

R = (CH₂)₂O(CH₂)₂

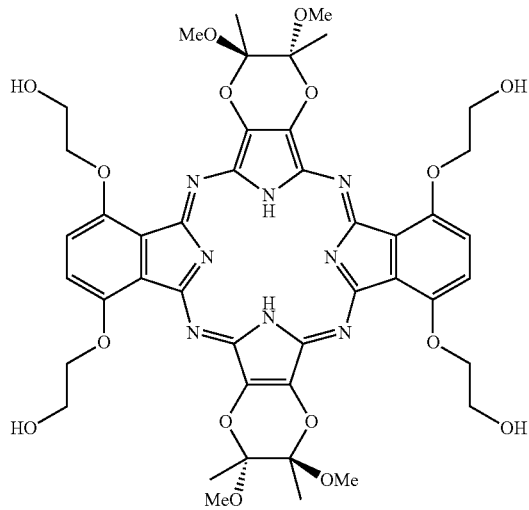

Compound 260

The present non-invasive pz compounds for use as diagnostic probes for tumor detection provide an important improvement in patient diagnosis and post-therapy monitoring of a cancer re-emergence and, accordingly, a reduction in mortality from cancer. The porphyrazines disclosed herein are porphyrin-like compounds that exhibit visible and NIR absorption/emission, and are preferentially accumulated and retained in tumor cell lines in vitro, as opposed to native cell lines.

Figure 2:
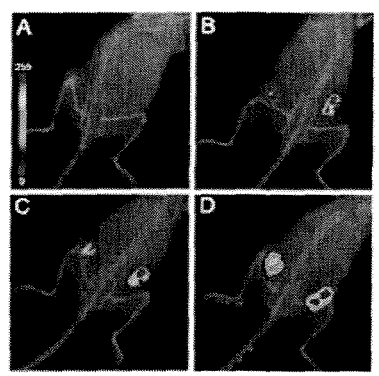
FIG. 2 contains intensity profiles of compound 247 accumulation over time in MDA-231 tumors in vivo after injection in tail vein (20 nmol), wherein fluorescent intensities are represented against anatomical x-ray images recorded simultaneously with a Kodak MM4000 multimodal imager at A) 5 hr, B) 24 hr, C) 32 hr, D) 48 hr (scaled as 0-255)

Experiments show that the present pz compounds a) exhibit intense optical absorbance and fluorescence in the visible and NIR window with optimum tissue penetration; and b) are selectively taken up by tumor cells (FIG. 1) and localize in tumors in vivo (FIG. 2). The flexible mode of synthesis of the pzs permits coupling of the pzs with non-pz chemotherapeutic agents which are currently used in the treatment of breast cancer and other cancers, as well as compounds in clinical evaluations, and MR relaxivity agents.

In particular, FIG. 1 shows that present compound 176 accumulates in A-549 lung carcinoma cells. FIG. 2 shows that compound 247 (20 nmol) accumulates over time (5 to 48 hours) in MDA-231 tumors in vivo after injection in tail vein.

Figure 3:
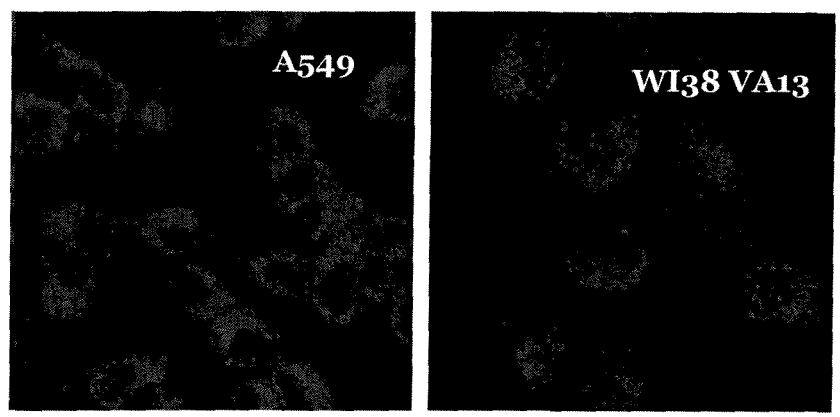
FIG. 3 is an NIR emission of compound 247, 50 μM, 24 hr stain (APD)
Figure 4:
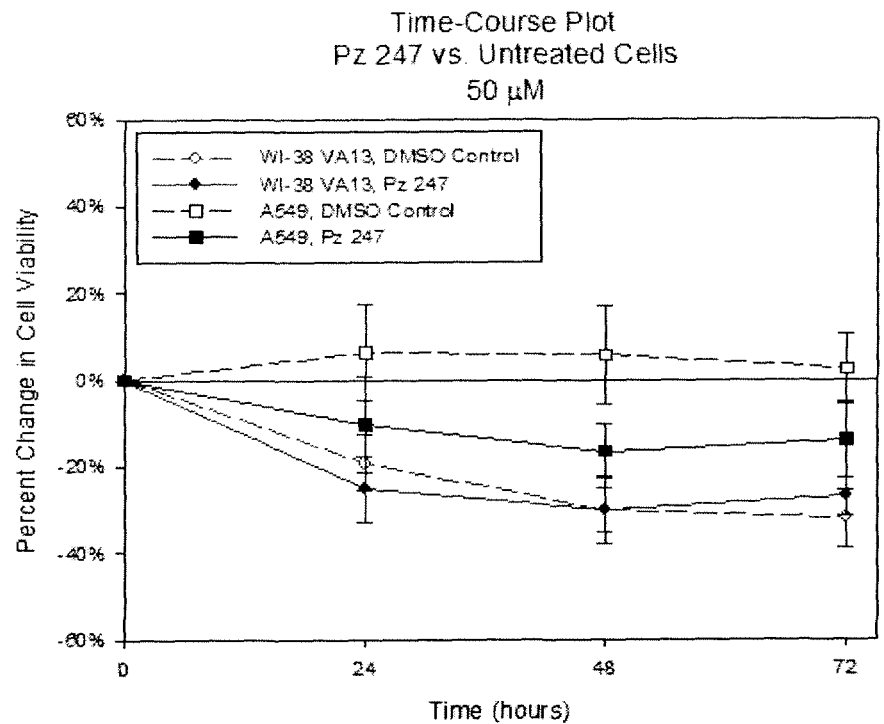
FIG. 4 is an MTT assay of compound 247, 50 μM.

Confocal microscopic images of the NIR fluorescence of compound 247 (FIG. 2) confirms its excellent uptake into A549 lung carcinoma cells and a lesser uptake into WI38 VA13 non-tumorigenic cells (FIG. 3). MTT tests for compound 247 show that it is non-toxic to non-tumorigenic cells (WI38 VA13), and mildly toxic to tumor cells (A549) (FIG. 4). The MTT test was performed using the procedure disclosed in S. Lee et al., *Metal-Based Drugs* (2008), pages 391-418.

Time course studies also were performed using compounds 241, 243, 244, 246, 247, 249, 254, and 255 using A549 lung carcinoma cells and W138 VA13 non-tumorigenic cells. The studies confirmed accumulation of a present pz in tumor cells and a decrease in tumor cell viability.

To demonstrate the pz biodistribution in mammals, tumor-bearing mice were injected with compound 247, which resulted in an unexpected tumor localization, as shown in FIG. 2. In one experiment, male FVB/n5 Rag-1-/- mice were injected with 5×105 PC3-EGFP (human prostate tumor cells stably expressing GFP) in the tibia four weeks prior to imaging with pzs. Prior to imaging, the mice were anesthetized with 4% isoflurane and injected with 20 nmol of compound 247 (150 μL, 7.5% DMSO) intravenously via the tail vein.

Figure 5:
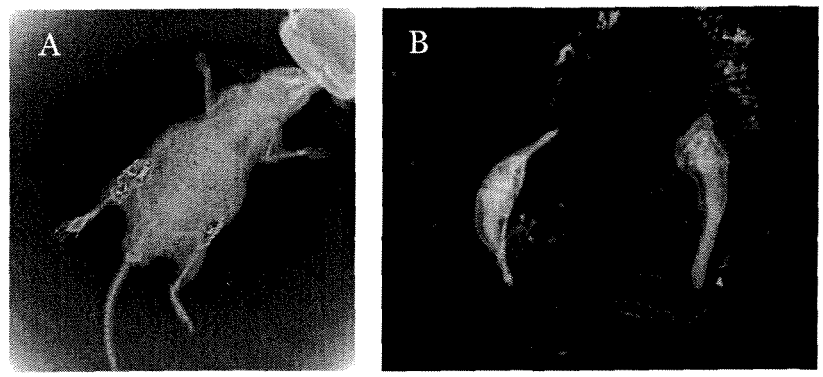
FIG. 5 A) is an image of 730 nm emission for compound 247 overlaid on X-ray image of FVB/n5 Rag1−/− male mouse with tumors in the tibia generated from the injection of PC3-EGFP cells, FIG. 5 B) is a superposition of images of 730 nm emission of compound 247 with 535 nm emission from GFP expressed in the tumor taken from excised legs with skin removed.

Fluorescent images were acquired immediately and after 4, 24, and 42 hours. Using an excitation band pass filter of 625 nm and a 700 nm emission bandpass filter, pz fluorescence was seen in the liver after 4 hours, but the pz was highly localized in the mouse tibia tumors after 24 hours (FIG. 5). GFP images were acquired using excitation wavelengths of 465 nm and fluorescence was detected at 535 nm. X-ray images were acquired for anatomical co-registration.

Figure 6:
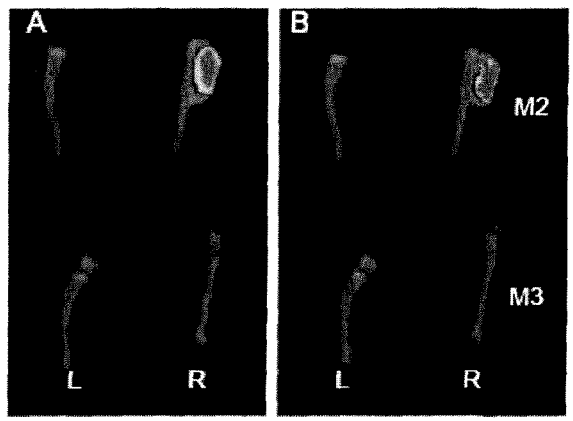
FIG. 6 shows excised tibial bones of mice injected with 20 nmol of compound 247. A) 535 nm GFP fluorescence of PC3-EGFP tumors with x-ray overlay and B) 730 nm NIR fluorescence of compound 247 with x-ray overlay.

The mice subsequently were euthanized, legs were excised, and images were acquired without the surrounding skin and muscle. Overlaid images of red fluorescence from the pz and green fluorescence from PC3-EGFP tumor cells (FIG. 5B) demonstrate that the red fluorescence from compound 247 is localized in the tumors. Tumor localization of compound 247 is reproducible, as GFP and pz fluorescence are both localized in the tumor, as seen for mouse 2 (M2) in FIG. 6. FIG. 6 shows excised tibial bones of mice injected with 20 nmol of compound 247, i.e., 535 nm GFP fluorescence of PC3-EGFP tumors with x-ray overlay (FIG. 6A) and 730 nm NIR fluorescence of compound 247 with x-ray overlay (FIG. 6B). Mouse 3 (M3) does not have a tumor, as indicated by the absence of GFP fluorescence. The absence of NIR fluorescence from the tibia of M3 indicates that pz is not non-specifically retained in the bones.

In a second experiment to verify that compound 247 robustly and reproducibly localizes in tumors of more than one tissue origin, female SCID mice were subcutaneously injected with MDA-MB-231-RFP cells stably expressing Red Fluorescent Protein (RFP). See FIGS. 2 and 7. This approach provides excellent confirming information because (a) palpable subcutaneous tumors are easily identified prior to imaging as opposed to bone tumors which are difficult to detect non-invasively; (b) RFP-expressing tumors are visible through the skin as opposed to GFP tumors, which require removal of skin prior to imaging; (c) pz localization in the tumor is visible during non-invasive whole animal imaging; and (d) tumors are easily harvested, fixed, and processed for histochemical and biochemical analyses.

Five mice were dosed with 20 nmol of compound 247 in 7.5% DMSO, administered intravenously. The emission wavelength used for RFP excitation was 535 nm with emission detected using a 565-615 nm bandpass filter. Compound 247 was excited using a 625 nm bandpass and emission detected at 700 nm. RFP fluorescent filters do not overlap with either excitation or emission of compound 247. Therefore, there is no penetration of undesired signal during imaging.

Figure 7:
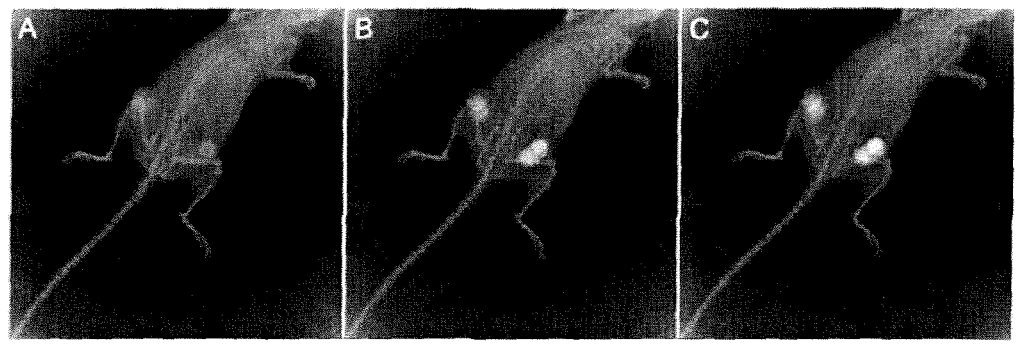
FIG. 7 contains live animal false-color fluorescent images of subcutaneously implanted MDA-MB-231 tumors stably expressing red fluorescent protein (RFP) and of compound 247, wherein images were acquired 48 hours after tail vein injection of 20 nmol compound 247: A) RFP fluorescence, B) compound 247 NIR fluorescence, C) merged RFP and compound 247 images illustrating co-localization in tumor.

Images were acquired for RFP, as well as pz fluorescence, after 5, 24, 32 and 48 hours. Pz fluorescence was detectable after as few as 5 hours, and intensity increased dramatically over the course of the 48 hour experiment, showing precise colocalization with the RFP fluorescence. In addition, there is no pz fluorescence in other mouse organs or tissues (FIGS. 2 and 7). With this remarkable contrast, compound 247 therefore acts as a 'turn-on' NIR-fluorescence tumor imager.

Figure 8:
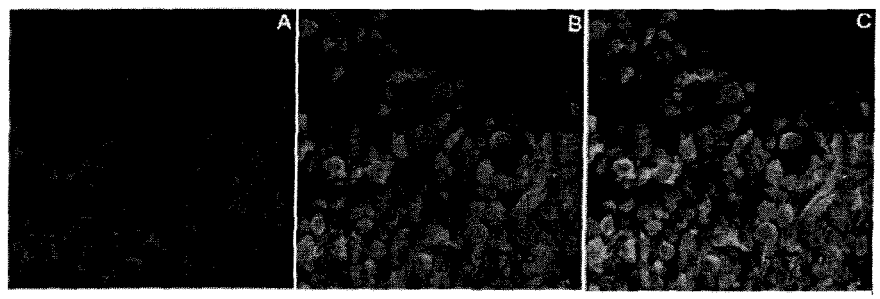
FIG. 8 shows colocalization of compound 247 and tumor from right-hand tumor of FIG. 7, 4-micron, paraffin-embedded section counter-stained with dapi for nuclei: A) overlay of dapi (two photon 720 nm excitation; 435 nm emission) and RFP (543 nm; 565-615 emission); B) overlay of dapi and compound 247 (633 nm; 650-715 nm); C) triple overlay of dapi, RFP and compound 247.

At the conclusion of the 48 hour experiment, the tumors were excised and processed for antibody staining. Slices were stained for nuclei (DAPI) to determine the localization of pzs within heterogeneous 3-dimensional tumors. The results in FIG. 8 definitively show precise colocalization of compound 247 with the tumor cytosol. The important benefit of having the RFP and pz survive tissue processing is noted.

In addition to acting as an NIR imaging agent, the present pzs also serve as a platform for multimodal optical-MR (magnetic resonance) contrast agents.

Dual-mode contrast agents were generated by coupling pz optical agents with gadolinium-based ($Gd^{3+}$) MR agents in order to permit co-registration of optical and MR image data. The synthetic versatility of the present pz structure allows a variety of strategies for attaching multiple MR imaging agents, for example, $Gd^{3+}$ chelates, to the pz structure. These new multimodal pz-based agents have two major advantages: (a) polymer based agents are not monodisperse, exhibit a range of molecular weights from 12,000 to 17,0000, and are difficult to characterize, and (b) the relaxivity of a $Gd^3$ chelate on the polymer is approximately the same as a single $Gd^{3+}$ chelate molecule (about 3 $mM^{-1}s^{-1}/Gd$). This indicates that free rotation of the $Gd^{3+}$ complex attached to the polymer, rather than overall tumbling of the polymer, dominates the effective rotational correlation time (R), and thus limits the relaxivity. The relaxivity of a $Gd^{3+}$ chelate attached to a pz ranges from about 10 to about 14 mM-1s-1/Gd (Table 1).

In the preparation of Gd-pzs, 'click' chemistry was used to append 4 and 8 $Gd^{3+}$ chelates to an $M[pz(A_2;B_2)]$ pz, leading to the Gd8-Mpz conjugate (M=Zn, Cu) shown above, and analogous Gd-4-Mpz conjugates having one chelate per pz 'arm'. As shown in Table 1, the molecular relaxivities ($r_1$) of the Gd-pzs are extremely high for low-molecular weight complexes, and much higher than that of a single Gd chelate, in contrast to the first-generation polymeric multi-Gd agents discussed above. This is significant because the higher the observed relaxivity of the conjugate, the greater its efficacy as an in vivo MR contrast agent. Importantly, these conjugates are suitable as dual-mode contrast agents because the presence of as many as eight Gd agents has no significant influence on the pz luminescence for the M=Zn complex. In addition, the pz-Gd conjugates are water soluble and can be administered to rodents without the addition of DMSO.

TABLE 1

| | Relaxivity ($r_1$, $mM^{-1}s^{-1}$) | | | |
|---|---|---|---|---|
| Compounds | MW (g/mol) | No. Gds | $r_1$/Gd | $r_1$ |
| Gd-DOTA[1] | 595.7 | 1 | 3.2 | 3.2 |
| Cu-Gd4-pz[1] | 3892.1 | 4 | 11.5 | 46 |
| Zn-Gd4-pz | 3893.9 | 4 | 10.5 | 42 |
| Cu-Gd8-pz | 6495.1 | 8 | 14.0 | 112 |
| Zn-Gd8-pz | 6496.9 | 8 | 12.8 | 102 |

[1]gadolinium tetrazacyclododecanetetraacetic acid

Figure 9:
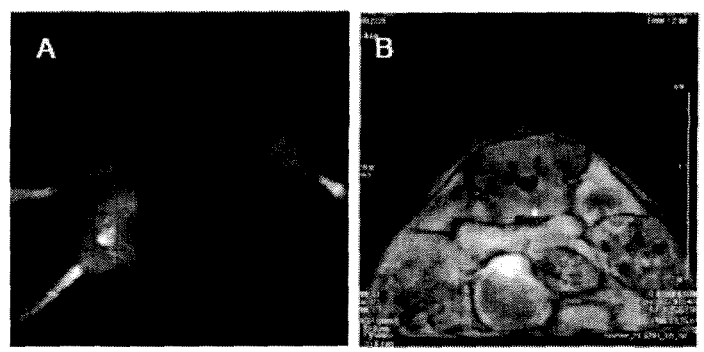
FIG. 9 contains NIR and MR imaging of a mouse injected with 60 nmol compound 262: A) NIR fluorescence of whole animal 0 hour after injection and B) T1-weighted MR image of mid-abdominal transverse slice of the mouse 2 hours after injection.

Injection of 20 nmol and 60 nmol of Gd8-Mpz into FVB/n5 Rag1−/− male mice showed it to be nontoxic. MR imaging two hours after injection of 60 nmol Gd8-Mpz clearly shows T1 image enhancement due to $Gd^{3+}$ in the kidneys and the bladder, but not the tumor, on a T1-weighted image acquired on a 4.7T small animal MR imaging magnet (FIG. 9). The long retention time of the Gd8-Mpz indicates that the compound can be used to illuminate the vasculature and for cardiovascular disease diagnosis. NIR emission was seen only from pzs in tumors. NIR fluorescence from Gd8 was not detected at even the highest concentration.

It is theorized that Gd8-pz does not effectively enter tumor tissue because it is too hydrophilic. Therefore, compound 270, a pz having a single appended $Gd^{3+}$, was synthesized. It was found that compound 270 is indeed taken up by live cells in culture, as shown by confocal fluorescence images, i.e., by WI38 VA13 cells stained with 50 μM of compound 270. Most significantly, the Gd chelate by itself does not accumulate in cells. Thus, a fluorescent pz attached to a Gd chelate can act both as a vector that facilitates preferential uptake of the MR agent into tumor cells and as a reporter that reveals the subcellular localization of the dual agent.

To test the MR properties of these pz-Gd compounds, WI38 VA13 cells were treated with 0, 50, and 100 μM of pz 270 and cell pellets were imaged on a 4.7T Bruker Biospec magnetic resonance imager. A large, concentration-dependent, MR contrast enhancement was shown by compound 270. The contrast-to-noise ratio (CNR) between pz-labeled and unlabeled cells is 26 for the 50 μM treatment and 40 for 100 μM. For reference, the clinically minimum detectable CNR is considered to be 3-5. This result establishes the Gd-pzs as multi-modal imaging agents.

As an example of optimizing the amphiphilicity and tumor uptake of compound 247 for use as an optical imaging agent, pz 260 was synthesized. Compound 260 contains the same six-membered chiral $[O-R]_2$ as compound 247, but has free hydroxyl moieties on $R^2$. Of additional importance, compound 260 provides one or more site for coupling to Gd chelates and to chemotherapeutic agents. In vitro experiments examine the effect of the change in amphiphilicity induced by this $R^2$ on the tumor-specific uptake of compound 247. Further modifications employ substituents such as, but not limited to, the following, when p is 0 to 10:

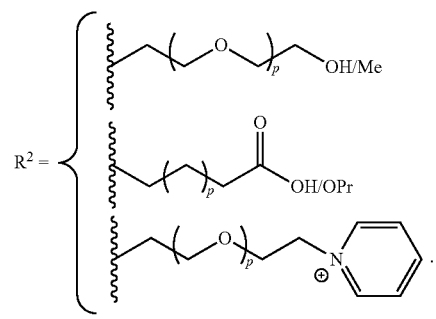

Click chemistry can be used to append $Gd^{3+}$ chelates to a pz for multimodal imaging applications. While the click coupling reaction is facile and high yielding, the copper catalyst metallates the core of a free-base ($M=H_2$) pz. The preferred fluorescent probes are free-base pzs (M=2H), and therefore an alternate approach for attaching the $Gd^{3+}$ chelates is shown in Scheme E. This approach involves tosylation of the terminal hydroxyl groups of compound 260, followed by coupling to an amino terminal $Gd^{3+}$ chelate. Sub-stoichiometric tosylation of the pz allows a variable number (e.g., 1-4) of $Gd^{3+}$ chelates.

Scheme E

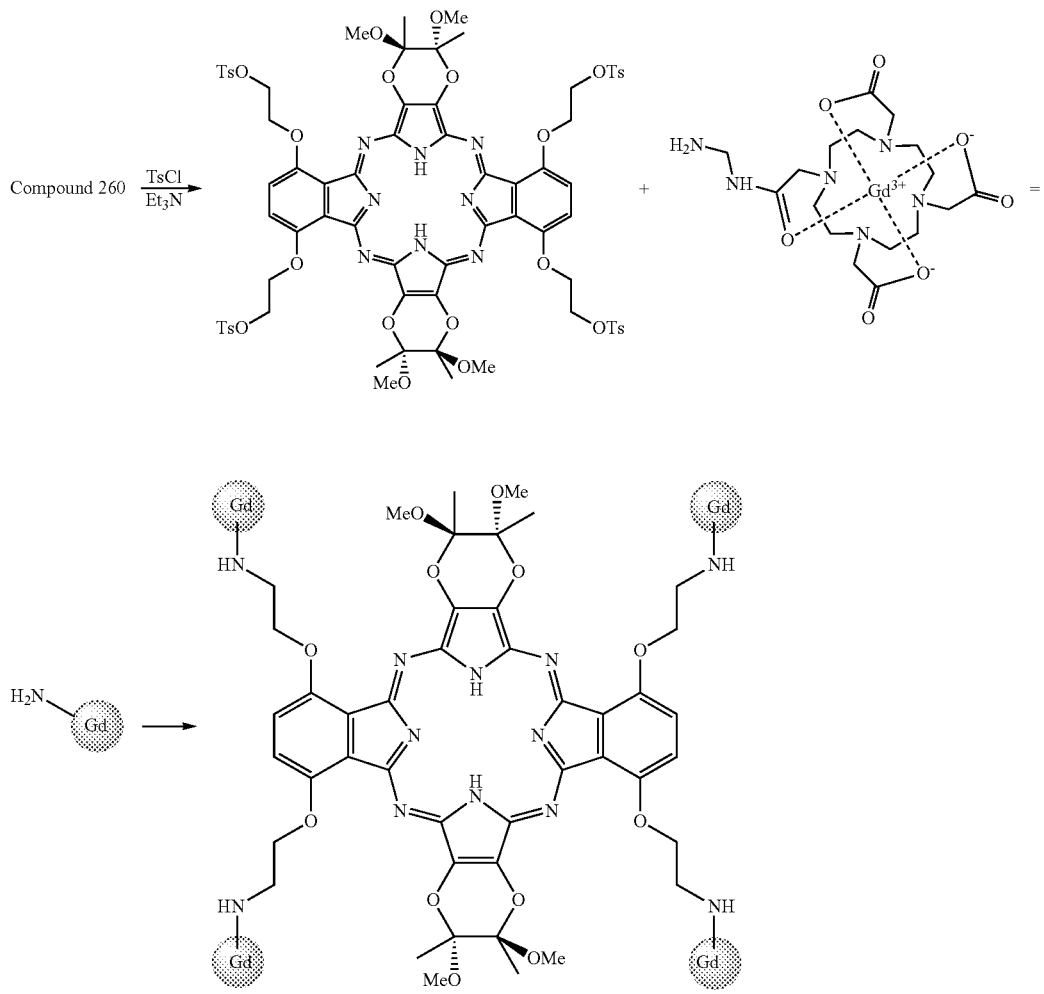

Analogous to appending a Gd$^{+3}$ complex to a present pz compound, a non-pz chemotherapeutic agent can be linked to a present pz compound. A present pz compound having an active —CO$_2$H, —OH, —SH, and/or —NH$_2$ group, for example, on a moiety of the pz can be coupled to a non-pz chemotherapeutic agent having a functional group, such as —NH, or —CO$_2$H, capable of linking with the active group of the pz.

The resulting pz-chemotherapeutic conjugate enhances the efficacy of the chemotherapeutic agent because the pz compound localizes the chemotherapeutic agent in the tumor. Localizing the chemotherapeutic agent at the tumor also reduces the severity of adverse side effects on normal tissue.

An example of this tumor targeting strategy is to conjugate the anti-tumor drug, doxorubicin, to a pz compound having one or more chemically reactive group. There are many alternate conjugation strategies to link the pz with the amino group of doxorubicin. One example is starting with compound 260 and using a procedure corresponding to Scheme E to attach one to four chemotherapeutic drug molecules to compound 260.

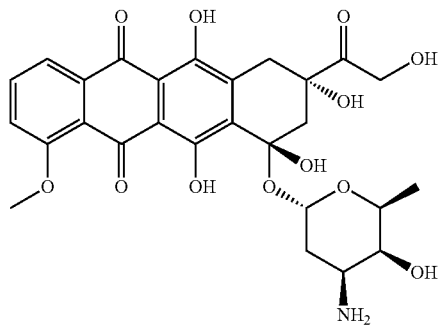

Doxorubicin

Additional chemotherapeutic agents having a functional group capable of conjugating with a pz include, but are not limited to, methotrexate, aminoglutethimide, aromasin, chlorambucil, cytarabine, dacarbazine, dactinomycin, melphalan, procarbazine, thioguanine, gemcitabine, idarubicin, epirubicin, daunorubicin, tamoxifen, taxotere, xeloda, and trimetrexate. Numerous additional chemotherapeutic agents listed below having a —CO$_2$H, —OH, —NH$_2$, or —SH group (or activated derivatives thereof, e.g., wherein a leaving group known in the art replaces a hydrogen atom of these groups) can be conjugated with a pz of the present invention.

The pzs of the present invention find use in optical and multi-mode imaging of tumors, including, but not limited to, breast, lung, skin, testicular, and other upper aerodigestive tumors, and as simultaneous imaging/anti-tumor agents that act as anti-tumor agents through direct tumor destruction and through photodynamic therapeutic applications. The pzs of the present invention find use as MR and NIR imaging agents, as PET (positron emission tomography) imaging agents, and as nuclear imaging agents. The pzs of the present invention find further use as therapeutic agents and simultaneous imaging/therapeutic agents whose therapeutic effects occur with or without light activation (photodynamic therapy), and with or without conjunction to a chemotherapeutic agent.

In one embodiment, the present invention provides methods of treating cancerous tumors comprising the administration of a present pz (with or without light activation) in conjunction with recognized anti-tumor modalities of surgery, radiotherapy, and chemotherapy. The effectiveness of a treatment can be measured in clinical studies or in model systems, such as a tumor model in mice or cell culture sensitivity assays. The present invention provides a combination therapy that results in improved effectiveness and/or reduced toxicity. Accordingly, in one embodiment, the invention relates to the use of a present pz in conjunction with, surgery radiotherapy or chemotherapy. A present pz also can be used alone in a method of treating a cancerous tumor, either with or without light activation. In one preferred embodiment, a non-pz chemotherapeutic agent is conjugated to the pz in order to target the tumor and concentrate the chemotherapeutic agent at the desired site of action and to allow for real-time, non-invasive monitoring of the tumor reduction during therapy and the monitoring and suppression of its reemergence.

When the combination therapy of the invention comprises administering a present pz with one or more additional anticancer agents, the pz and the additional anticancer agents can be administered to an individual concurrently or sequentially. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; any one or a combination of the additional anticancer agents listed below may be administered.

The present invention includes methods for treating cancer comprising administering to an individual in need thereof a present pz and one or more additional anticancer agents or pharmaceutically acceptable salts thereof. The pz and the additional anticancer agent can act additively or synergistically. Suitable anticancer agents include, but are not limited to, gemcitabine, capecitabine, methotrexate, taxol, taxotere, mereaptopurine, thioguanine, hydroxyurea, cyclophosphamide, ifosfamide, nitrosoureas, mitomycin, dacarbazine, procarbizine, etoposide, teniposide, campatheeins, bleomycin, doxorubicin, idarubicin, daunorubicin, dactinomycin, plicamycin, mitoxantrone, L-asparaginase, doxorubicin, epirubicin, 5-fluorouracil (5-FU), taxanes (such as docetaxel and paclitaxel), leucovorin, levamisole, irinotecan, estramustine, etoposide, nitrogen mustards, BCNU, nitrosoureas (such as carmustine and lomustine), platinum complexes (such as cisplatin, carboplatin and oxaliplatin), imatinib mesylate, hexamethylmelamine, topotecan, tyrosine kinase inhibitors, tyrphostins herbimycin A, genistein, erbstatin, and lavendustin A.

In one embodiment, the anti-cancer agent can be, but is not limited to, a drug selected from the group consisting of alkylating agents, nitrogen mustards, cyclophosphamide, trofosfamide, chlorambucil, nitrosoureas, carmstine (BCNU), lomustine (CCNU), alkylsulphonates, busulfan, treosulfan, triazenes, plant alkaloids, vinca alkaloids (vineristine, vinblastine, vindesine, vinorelbine), taxoids, DNA topoisomcrase inhibitors, epipodophyllins, 9-aminocamptothecin, camptothecin, crisnatol, mitomycins, mitomycin C, anti-metabolites, anti-folates, DHFR inhibitors, trimetrexate, IMP dehydrogenase inhibitors, mycophenolic acid, tiazofurin, ribavirin, EICAR, ribonucleotide reductase inhibitors, hydroxyurea, deferoxamine, pyrimidine analogs, uracil analogs, floxuridine, doxifluridine, ratitrexed, cytosine analogs, cytarabine (araC), cytosine arabinoside, fludarabine, purine analogs, mercaptopurine, thioguanine, DNA antimetabolites, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole (inosine glycodia)dehyde), macebecin II, pyrazoloimidazole, hormonal therapies, receptor antagonists, anti-estrogen, tamoxifen, raloxifene, megestrol, LHRH agonists, goserelin, leuprolide acetate, anti-androgens, flutamide, bicalutamide, retinoids/deltoids, cis-retinoic acid, vitamin A derivative, all-trans retinoic acid (ATRA-IV), vitamin D3 analogs, El) 1089, CB 1093, ICH 1060, photodynamic therapies, vertoporfin, BPD-MA, phthalocyanine, photosensitizer Pc4, demethoxy-hypocrellin A (2BA-2-DMHA), cytokines, interferon-a, interferon-I3, interferon-y, tumor necrosis factor, angiogenesis inhibitors, angiostatin (plasminogen fragment), antiangiogenic antithrombin UI, angiozyme, ABT-627, Bay 12-9566, benefin, bevacizumab, BMS-275291, cartilage-derived inhibitor (CDI), CAI, CD59 complement fragment, CEP-7055, Col 3, combretastatin A-4, endostatin (collagen XVIII fragment), fibronectin fragment, Gro-beta, halofuginone, heparinases, heparin hexasaccharide fragment, HMV833, human chorionic gonadotropin (hCG), IM-862, interferon inducible protein (IP-10), interleukin-12, kringle 5 (plasminogen fragment), marimastat, metalloproteinase inhibitors (UMPs), 2-methoxyestradiol, MMI 270 (CGS 27023A), MoAb IMC-I C11, neovastat, NM-3, panzem, P1-88, placental ribonuclease inhibitor, plasminogen activator inhibitor, platelet factor-4 (PF4), prinomastat, prolactin 161(D fragment, proliferin-related protein (PRP), PTK 787/ZK 222594, retinoids, solimastat, squalamine, SS 3304, SU 5416, SU 6668, SU 11248, tetrahydrocortisol-S, tetrathiomolybdate, thalidomide, thrombospondin-1 (TSP-1, TNP-470, transforming growth factor-beta (TGF-11), vasculostatin, vasostatin (calreticulin fragment), ZD 6126, ZD 6474, farnesyl transferase inhibitors (FTI), bisphosphonates, antimitotic agents, allocolchicine, halichondrin B, colchicine, colchicine derivative, dolstatin 10, maytansine, rhizoxin, thiocolchicine, trityl cysteine, isoprenylation inhibitors, dopaminergic neurotoxins, 1-methyl-4-phenylpyridinium ion, cell cycle inhibitors, staurosporine, actinomycins, actinomycin D, dactinomycin, bleomycins, bleomycin A2, bleomycin B2, peplomycin, anthracycline, adriamycin, epirubicin, pirarnbicin, zorubicin, mitoxantrone, MDR inhibitors, verapamil, $Ca^{2+}$ATPase inhibitors, and thapsigargin.

Other anti-cancer agents that may be used in the present invention include, but are not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelcsin; bleomycin sulfate; brequinar sodium; bropirimine; busul fan; cactinomycin; calusterone; caracemide; carbetimer; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mecchlorethamine hydrochloride; megestrol acetate; melengestrol acetate; melphalan; menogaril; mercaptopurine; methotrexate sodium; metoprine; meturedepa; mitindomide; mitocarcin; mitocromin; mitogillin; mitomalcin; mitomycin; mitusper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsornycin; spirogermanium hydrochloride; spiromustine; spiroplatin; streptonigrin; streptozocin; sulofenur; talisomycin; tecogalan sodium; tegafur; teloxantrone hydrochloride; temoporfin; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracit mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozolc; zeniplatin; zinostatin; zorubicin hydrochloride.

Further chemotherapeutic agents that can be used in the present invention include, but are not limited to: 20-epi-1,25-dihydroxyvitamin D3; 5-ethynyluracil; abiraterone; aclarubicin; acylfulvene; adecypenol; adozelesin; aldesleukin; ALL TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein 1; antiandrogen, prostatic carcinoma; antiestrogen; antineoplaston; antisense oligonucleotides; aphidicolin glycinate; apoptosis gene modulators; apoptosis regulators; apurinic acid; ara CDP DL PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR-JABL antagonists; benzochlorins; benzoylstaurosporine; beta lactam derivatives; beta alethine; betaclarnycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; carboxamide amino triazole; carboxyamidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexveraparnil; diaziquone; didemnin B; didox; diethylnorsperniine; dihydro 5 azacytidine; dihydrotaxol, 9; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fltidarabine; fluorodaunoruniein hydrochloride; forfenimex; formestane; fostriecin; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubiein; ipomeanol, 4; iroplact; irsogladine; isobengazole; isohomohalicondrin B; itasetron; jasplakinolide; kahalalide F; larnellarin N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1 based therapy; mustard anti-cancer agent; mycaperoxide B; mycobacterial cell wall extract; myriaporone; N acetyldinaline; N substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum triamine complex; porfimer sodium; porfiromycin; prednisone; propyl his acridone; prostaglandin J2; proteasome inhibitors; protein A based immune modulator; protein kinase C inhibitor; protein kinase C inhibitors, microalgal; protein tyrosine phosphatase inhibitors; purine nucleoside phosphorylase inhibitors; purpurins; pyrazoloaeridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RH retinamide; rogletimide; rohitukine; romurtide; roquinimex; rubiginone BI; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hoimone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Any of the above-identified chemotherapeutic agents having a reactive functional group as disclosed above can be conjugated to a pz of the present invention to provide a conjugate of pz and a chemotherapeutic agent that localizes in a tumor. Additionally, the invention provides methods of treating a cancer using a present pz as an alternative to chemotherapy alone or radiotherapy alone where the chemotherapy or the radiotherapy has proven or can prove too toxic, e.g., results in unacceptable or unbearable side effects, for the subject being treated.

In the present method, a therapeutically effective amount of a present pz or pz conjugate, typically formulated in accordance with pharmaceutical practice, is administered to a human being in need thereof. A present pz or pz conjugate can be administered by any suitable route.

Pharmaceutical compositions include those wherein a present pz or pz conjugate is present in a sufficient amount to be administered in an effective amount to achieve its intended purpose. The exact formulation, route of administration, and dosage is determined by an individual physician in view of the specific tumor of interest.

The pzs of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing and administration of the pz.

The term "carrier" refers to a diluent, adjuvant, or excipient, with which a present pz is administered. Such pharmaceutical carriers can be liquids, such as water and oils, including those of petroleum, animal, vegetable or synthetic origin, such as peanut oil, soybean oil, mineral oil, sesame oil, and the like. In addition, auxiliary, stabilizing, thickening, and lubricating agents can be used. The pharmaceutically acceptable carriers are sterile. Water is a preferred carrier when the pz is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, emulsifying, entrapping, or lyophilizing processes. Proper formulation is dependent upon the route of administration chosen. When administered in liquid form, a liquid carrier, such as water, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present pz.

When a therapeutically effective amount of a present pz is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. The pz can be infused with other fluids over a 10-30 minute span or over several hours.

A present pz can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present pz can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a pz and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration, for example, a syringe, drip bag, or patch. In another embodiment, pz is a lyophilate. In this instance, the kit can further comprise an additional container which contains a solution useful for the reconstitution of the lyophilate.

REFERENCES (1) M. J. Fuchter et al., *Aust. J. Chem.* 2008, 61, 235-255.
(2) N. D. Hammer et al., *J. Med. Chem.* 2005, 48, 8125-8133.
(3) B. J. Vesper et al., *Photochem. Photohiol., B* 2006, 82, 180-186.
(4) A. Sholto et al., *Photochem. Photobiol.* 2008, 84, 764-773.

What is claimed:

1. A method of imaging a tumor comprising:
    a) administering a sufficient amount of a porphyrazine for visualization to a mammal suspected of having a tumor; and
    b) imaging the porphyrazine in the mammal,
    wherein the porphyrazine has a structure

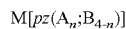

wherein pz is

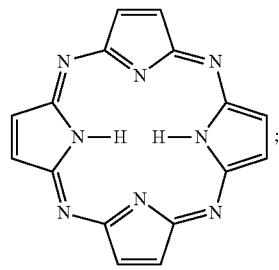 [SMILES: C1=Cc2nc1nc1ccc(nc3nc(nc4ccc(n2)[nH]4)C=C3)[nH]1]

M is 2H or a metal ion capable of complexing with pyrrole nitrogen atoms;
n is 1-3;
A is $(-N(R^1)_2)_2$, $(-OR^1)_2$, or $(-SR^1)_2$;
B is a benzo ring fused on the pz, substituted with one or more $-XR^2$, group, wherein X is O or S;
$R^1$, independently, and $R^2$, independently, are selected from the group consisting of $C_{1-6}$alkyl optionally substituted with OH, $OR^3$, $N(R^3)_2$, $CO_2R^3$, or $CON(R^3)_2$, $C_{3-6}$cycloalkyl optionally substituted with OH, $OR^3$, $N(R^3)_2$, $CO_2R^3$, or $CON(R^3)_2$, $(CH_2)_{1-3}C_{3-6}$cycloalkyl optionally substituted with OH, $OR^3$, $N(R^3)_2$, $CO_2R^3$, or $CON(R^3)_2$, $(CH_2)_{1-6}C_6H_5$, optionally substituted with OH, $OR^3$, $N(R^3)_2$, $CO_2R^3$, or $CON(R^3)_2$, wherein each $R^3$, independently is H, $C_{1-6}$alkyl, $C_{3-6}$cycloalkyl, or $(CH_2)_{1-3}C_{3-6}$cycloalkyl;

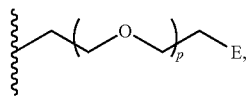

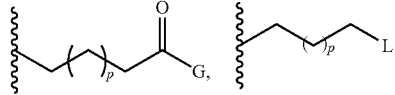

p is 0-10;
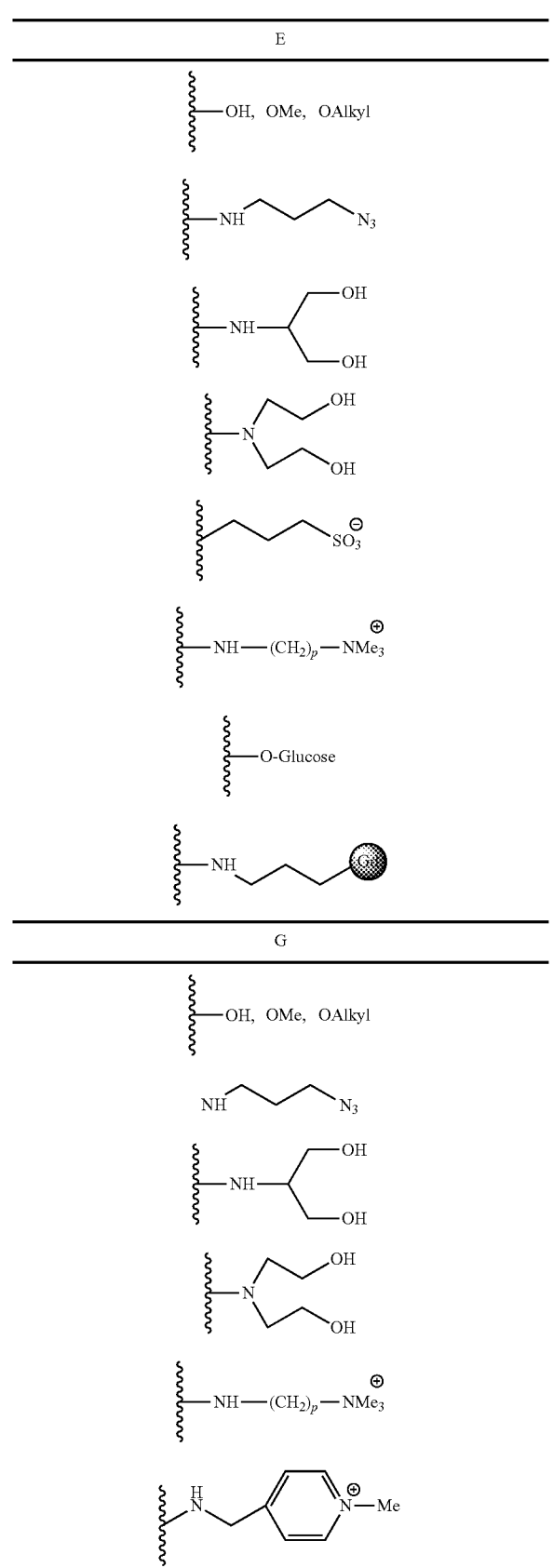
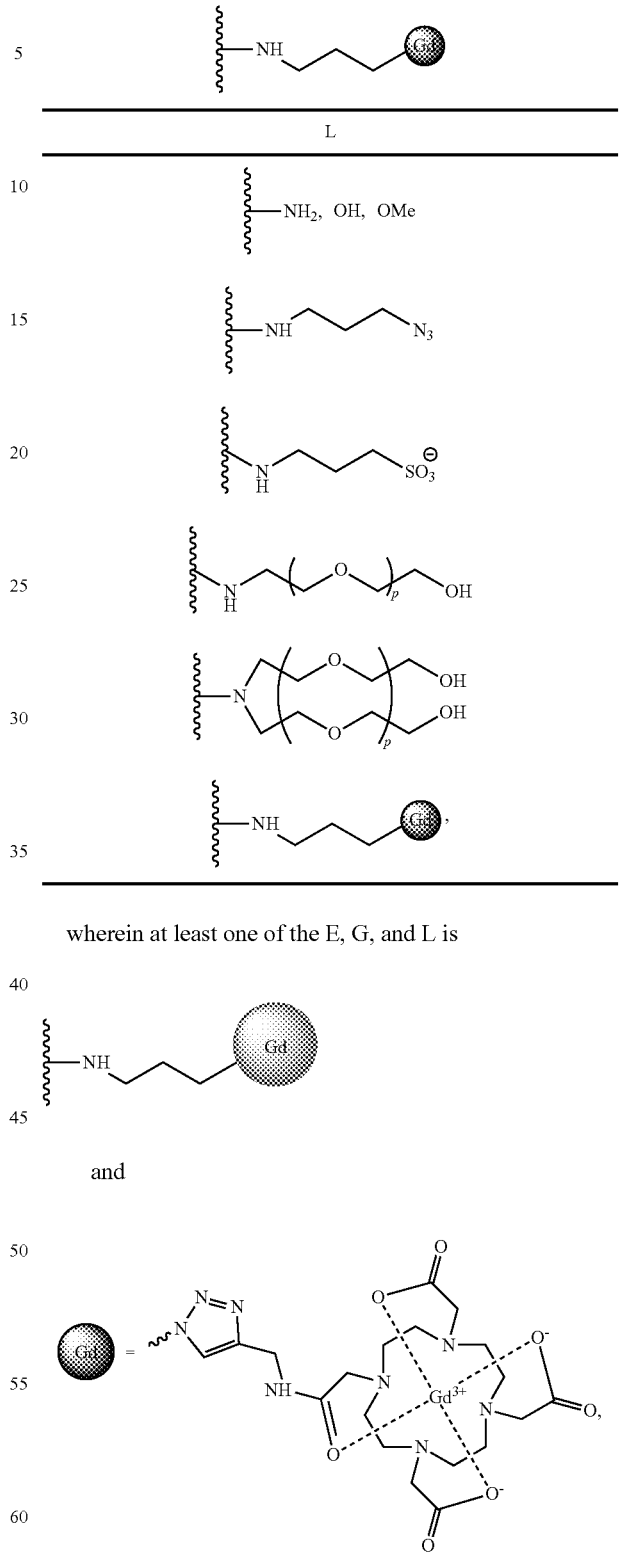
wherein at least one of the E, G, and L is
and
or two $R^1$, groups can be taken together to form a 5- or 6-membered ring, and the porphyrazine localizes at a tumor in the mammal, and the porphyrazine comprises one to eight Gd chelates and the imaging is selected from the group consisting of optical imaging, visible or NIR imaging, PET imaging, nuclear imaging, and MR imaging.

2. The method of claim 1 wherein the porphyrazine is chiral.

3. The method of claim 1 wherein A is, independently, $(-OR^1)_2$, or $(-SR^1)_2$.

4. The method of claim 1 wherein the porphyrazine has a Structure $M[pz(A_2; B_2)]$.

5. The method of claim 4 wherein the porphyrazine has a structure $M[pz(transA_2; B_2)]$.

6. The method of claim 1 wherein M is selected from the group consisting of two hydrogen atoms, an alkali metal, an alkaline earth metal, a transition metal, a lanthanide, and an actinide.

7. The method of claim 1 wherein M is selected from the group consisting of nickel, copper, two hydrogen atoms, magnesium, iron, aluminum, manganese, gadolinium, rhodium, gold, cobalt, platinum, palladium, ruthenium, lead, lithium, zinc, chromium, technetium, silicon, indium, thallium, germanium, tin, tungsten, rhenium, zirconium, iridium, uranium, vanadium, titanium, molybdenum, gallium, neodymium, and ytterbium.

8. The method of claim 1 wherein said porphyrazine has the structure selected from the group consisting of

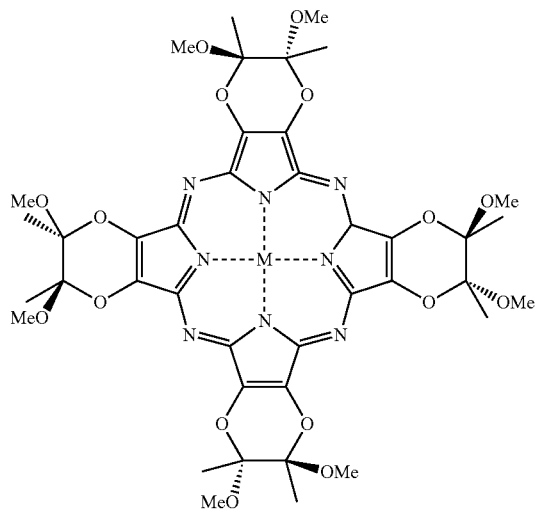
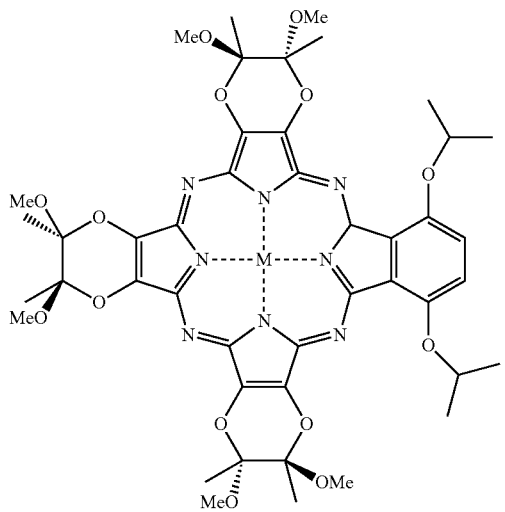
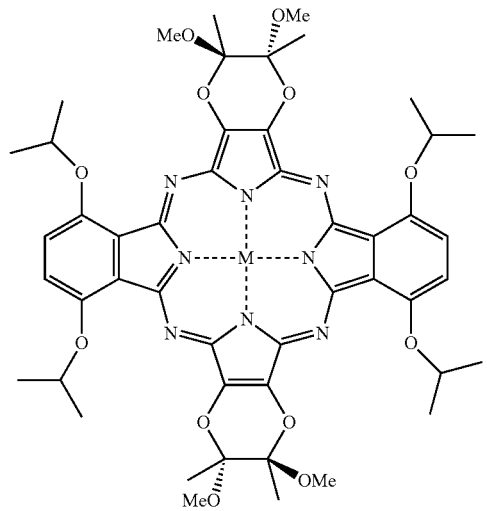
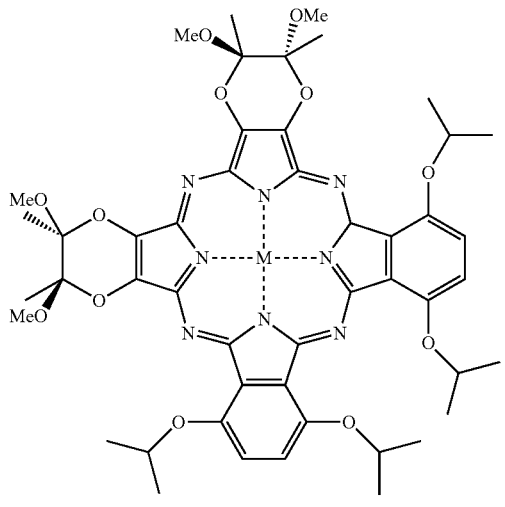

-continued
37
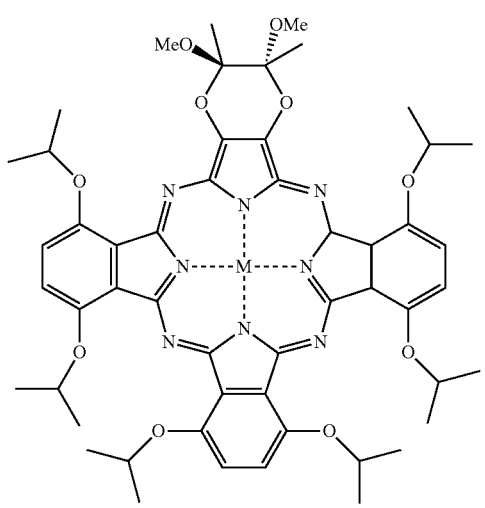
38
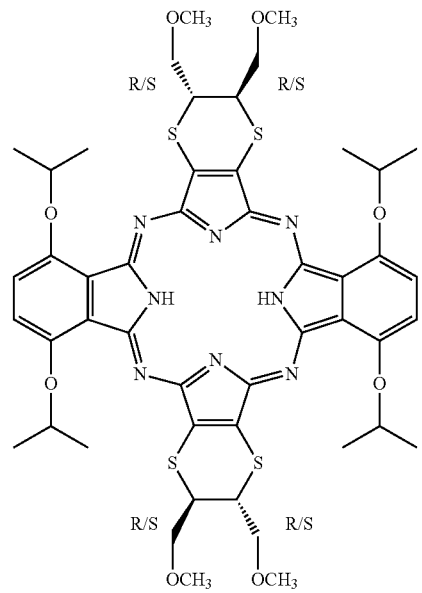
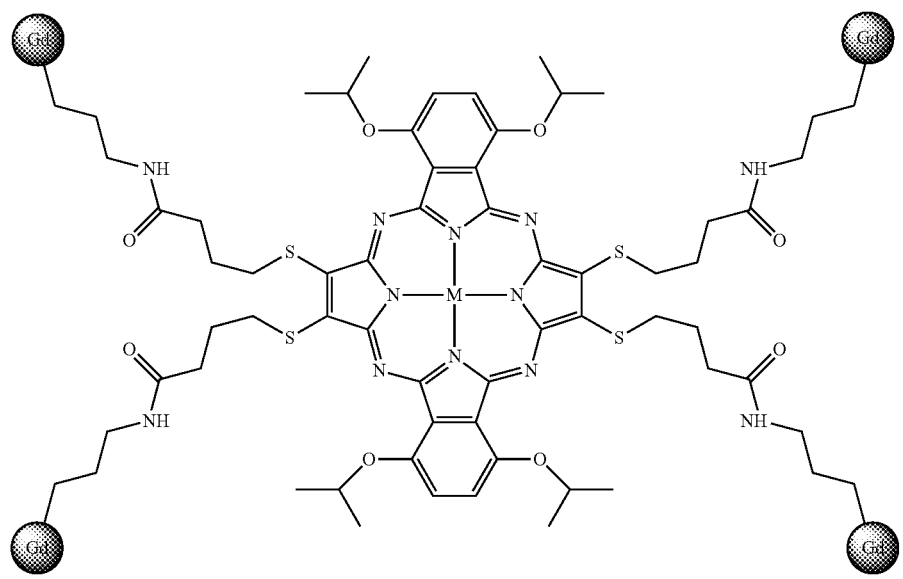
M = Zn(II)
M = Cu(II)

-continued
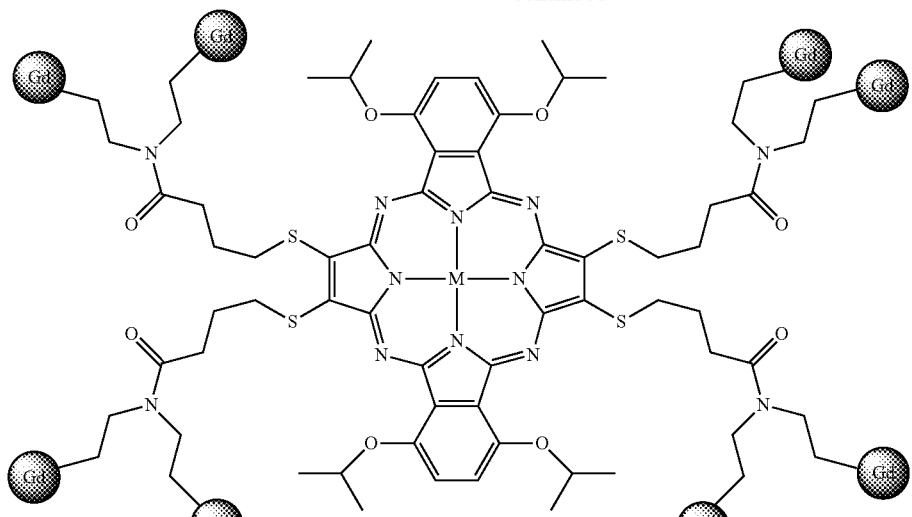
M = Zn(II)
M = Cu(II)
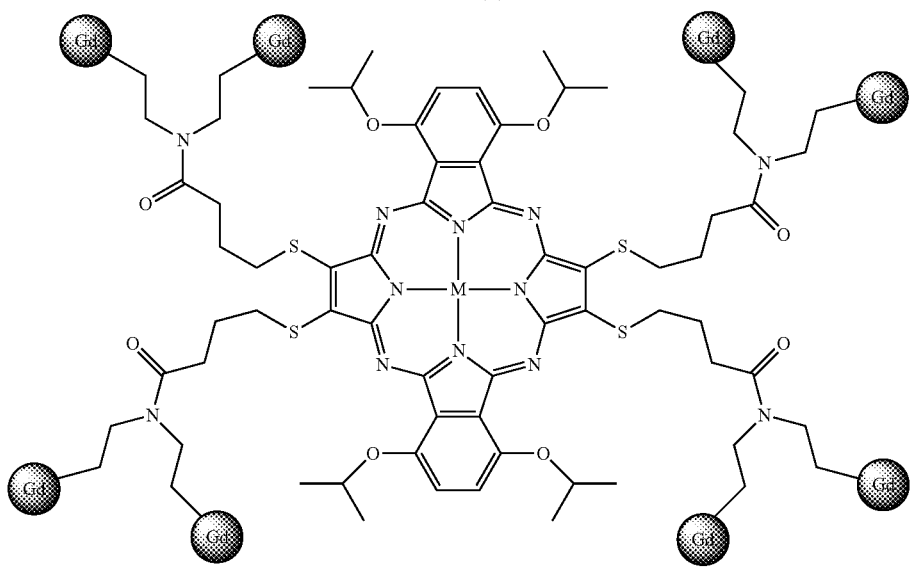
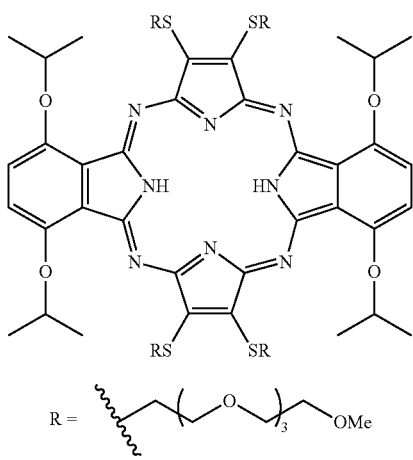
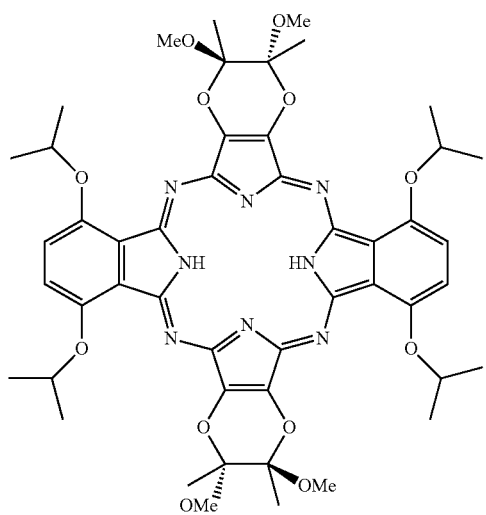

-continued

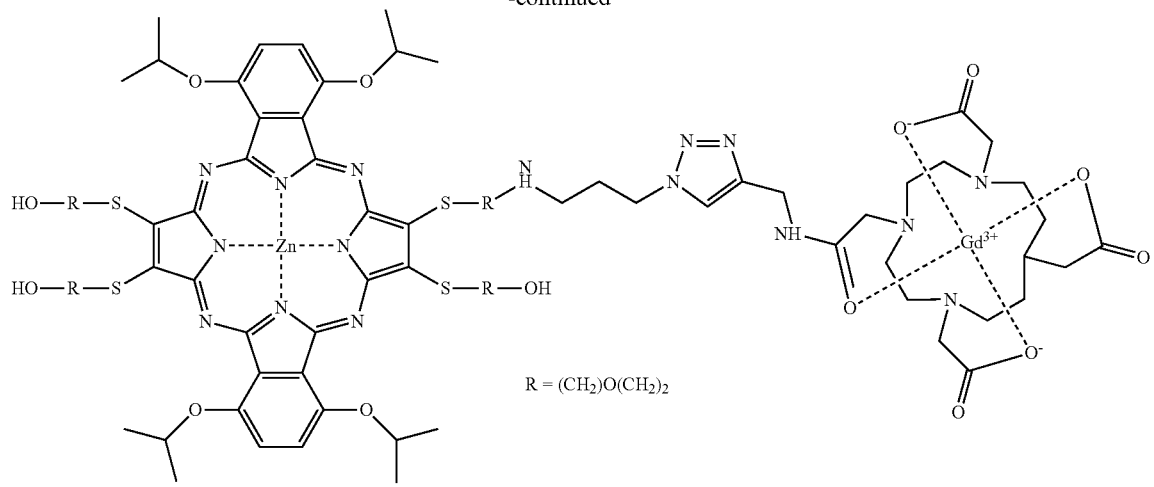

R = (CH$_2$)O(CH$_2$)$_2$

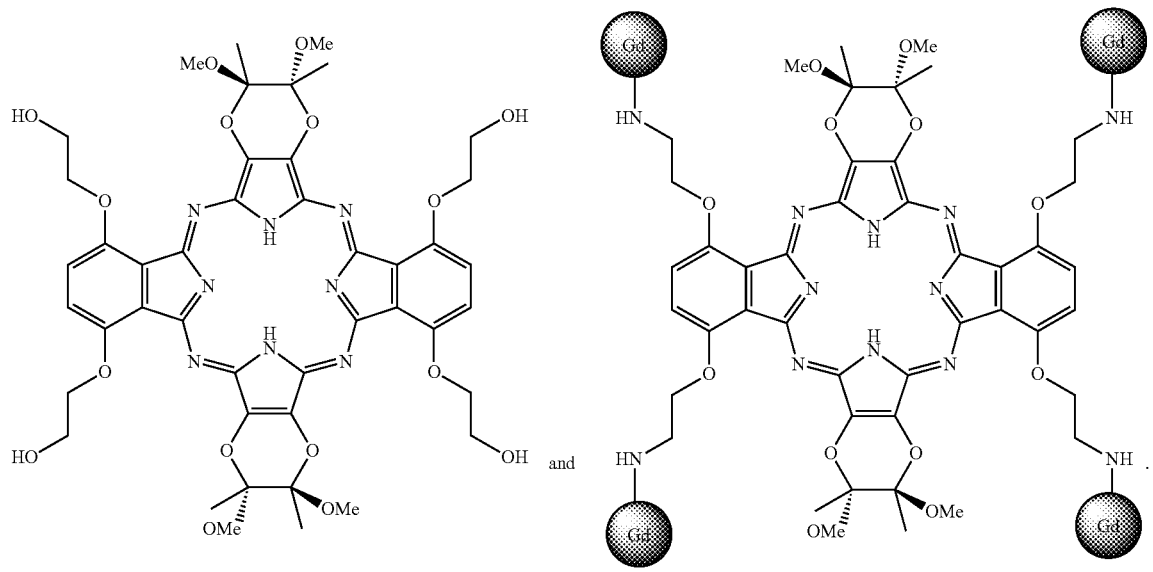

9. The method of claim 1 wherein the porphyrazine kills cells in the tumor.

10. The method of claim 9 further comprising the step of light activation of the porphyrazine.

11. The method of claim 1 wherein two or more visualizing methods are jointly or simultaneously used after administration of a single porphyrazine.

12. The method of claim 11 wherein the two or more imaging methods are optical and MR imaging or optical and PET imaging.

13. The method of claim 1 wherein the mammal is a human.

14. A porphyrazine-chemotherapeutic agent conjugate comprising a porphyrazine compound having a structure M[pz(A$_n$;B$_{4-n}$)]

wherein pz is

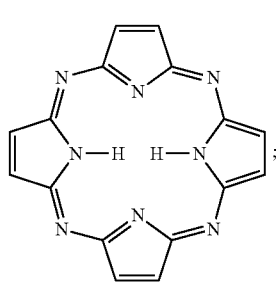 [SMILES: C1=Cc2nc1nc1ccc(nc3nc(nc4ccc(n2)[nH]4)C=C3)[nH]1]

M is 2H or a metal ion capable of complexing with pyrrole nitrogen atoms;

n is 1-3;

A is (—N(R$^1$)$_2$)$_2$, (—OR$^1$)$_2$, or (—SR$^1$)$_2$;

B is a benzo ring fused on the pz, substituted with one or more —XR$^2$, group, wherein X is O or S;

$R^1$, independently, and $R^2$, independently, are selected from the group consisting of $C_{1-6}$alkyl optionally substituted with OH, $OR^3$, $N(R^3)_2$, $CO_2R^3$, or $CON(R^3)_2$, $C_{3-6}$cycloalkyl optionally substituted with OH, $OR^3$, $N(R^3)_2$, $CO_2R^3$, or $CON(R^3)_2$, $(CH_2)_{1-3}C_{3-6}$cycloalkyl optionally substituted with OH, $OR^3$, $N(R^3)_2$, $CO_2R^3$, or $CON(R^3)_2$, $(CH_2)_{1-6}C_6H_5$, optionally substituted with OH, $OR^3$, $N(R^3)_2$, $CO_2R^3$, or $CON(R^3)_2$, wherein each $R^3$, independently is H, $C_{1-6}$alkyl, $C_{3-6}$cycloalkyl, or $(CH_2)_{1-3}C_{3-6}$cycloalkyl;

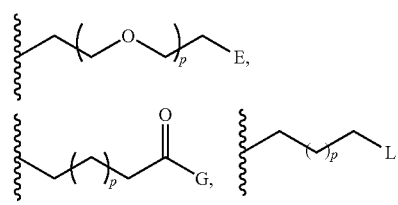

p is 0-10;

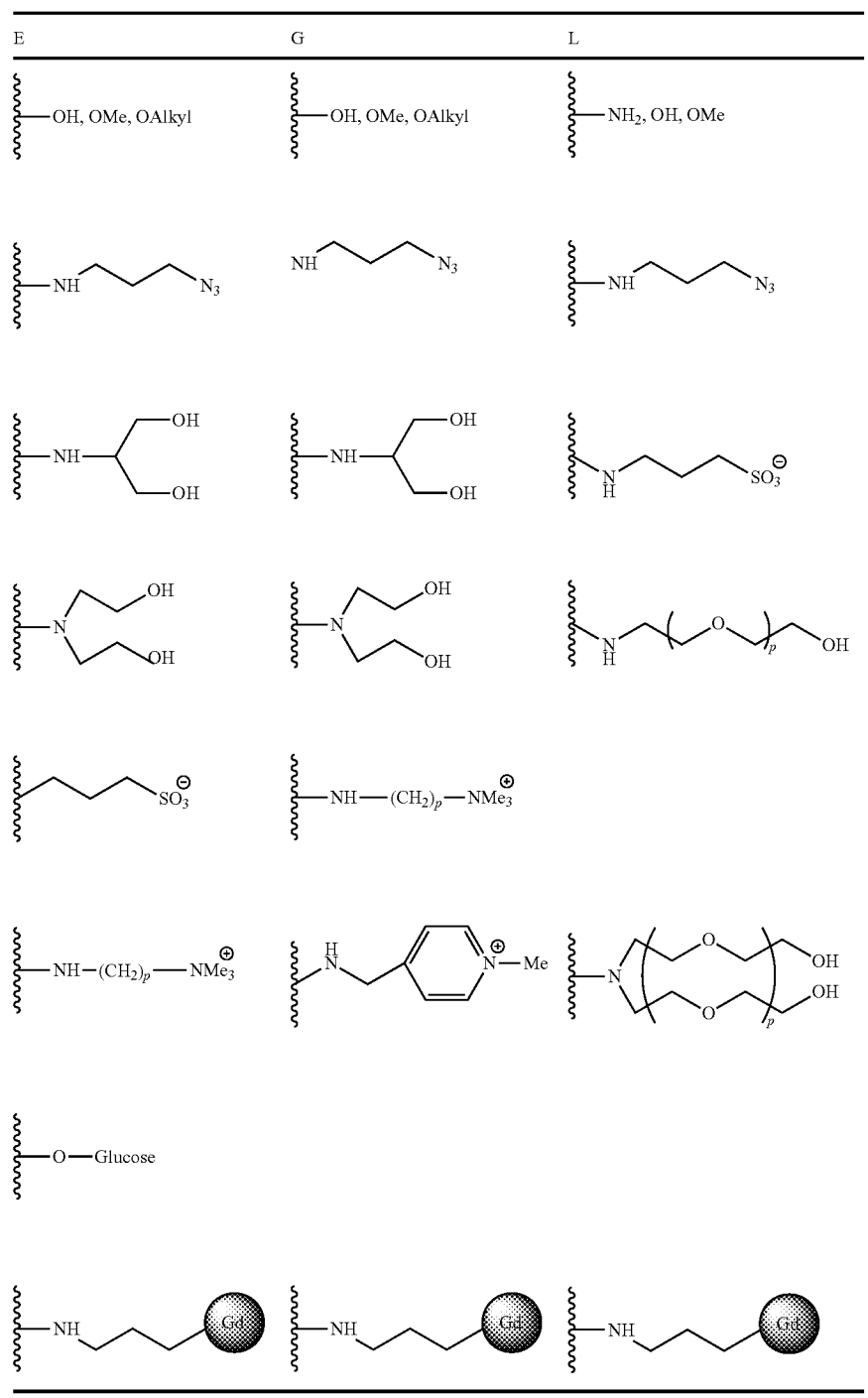

wherein at least one of E, G, and L is

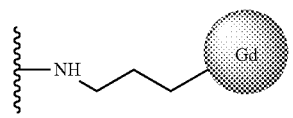

and

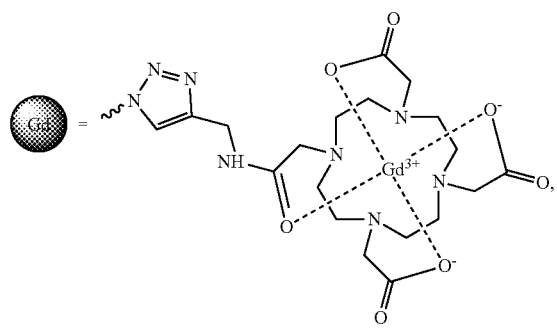

or two $R^1$, groups can be taken together to form a 5- or 6-membered ring and the porphyrazine comprises one to eight Gd chelates, linked to a chemotherapeutic agent selected from the group consisting of gemcitabine, capecitabine, methotrexate, taxol, taxotere, mereaptopurine, thioguanine, hydroxyurea, ifosfamide, nitrosoureas, mitomycin, procarbizine, etoposide, teniposide, campatheeins, bleomycin, doxorubicin, idarubicin, daunorubicin, plicamycin, mitoxantrone, doxorubicin, epirubicin, leucovorin, levamisole, irinotecan, estramustine, etoposide, nitrogen mustards, topotecan, genistein, erbstatin, and lavendustin A, alkylating agents, nitrogen mustards, cyclophosphamide, trofosfamide, chlorambucil, nitrosoureas, treosulfan, plant alkaloids, vinca alkaloids, vineristine, vinblastine, vindesine, vinorelbine, epipodophyllins, 9-aminocamptothecin, camptothecin, crisnatol, mitomycins, mitomycin C, anti-metabolites, anti-folates, trimetrexate, mycophenolic acid, tiazofurin, ribavirin, ribonucleotide reductase inhibitors, hydroxyurea, deferoxamine, pyrimidine analogs, floxuridine, doxifluridine, ratitrexed, cytarabine (ara C), cytosine arabinoside, fludarabine, purine analogs, mercaptopurine, thioguanine, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole (inosine glycodialdehyde), macebecin II, receptor antagonists, anti-estrogen, raloxifene, megestrol, LHRH agonists, goserelin, leuprolide acetate, anti-androgens, flutamide, bicalutamide, retinoids/deltoids, cis-retinoic acid, all-trans retinoic acid (ATRA-IV), CB 1093, vertoporfin, phthalocyanine, photosensitizer Pc4, angiogenesis inhibitors, antiangiogenic antithrombin UI, angiozyme, ABT-627, Bay 12- 9566, bevacizumab, BMS-275291, CAI, CD59, complement fragment, CEP-7055, Col 3, combretastatin A-4, endostatin (collagen XVIII fragment), fibronectin fragment, halofuginone, heparin hexasaccharide fragment, HMV833, IM-862, marimastat, metalloproteinase inhibitors (UMPs), 2-methoxyestradiol, MMI 270, (CGS 27023A), NM-3, panzem, platelet factor-4, (PF4), prinomastat, prolactin 161(D fragment, proliferin-related protein (PRP), PTK 787/ZK 222594, retinoids, solimastat, squalamine, SS 3304, SU 5416, SU 6668, SU 11248, tetrahydrocortisol-S, thalidomide, thrombospondin-1, (TSP-1), TNP-470, antimitotic agents, halichondrin B, trityl cysteine, 1-methyl-4-phenylpyridinium ion, staurosporine, bleomycins, bleomycin A2, bleomycin B2, peplomycin, anthracycline, adriamycin, epirubicin, pirarnbicin, zorubicin, mitoxantrone, MDR inhibitors, Ca2'ATPase inhibitors, thapsigargin, acivicin; aclarubicin; acodazole hydrochloride; adozelesin; arnbomycin; ametantrone acetate; aminoglutethimide; amsacrine; anthramycin; azacitidine; azotomycin; batimastat; bicalutamide; bisantrene hydrochloride; bisnafide dimesylate; bizelcsin; bleomycin sulfate; brequinar sodium; bropirimine; busul fan; cactinomycin; calusterone; carbetimer; carubicin hydrochloride; carzelesin; cedefingol; chlorambucil; cladribine; crisnatol mesylate; cytarabine; dacarbazine; daunorubicin hydrochloride; decitabine; diaziquone; docetaxel; doxorubicin hydrochloride; duazomycin; edatrexate; eflomithine hydrochloride; elsamitrucin; epirubicin hydrochloride; erbulozole; esorubicin hydrochloride; estramustine; estramustine phosphate sodium; etanidazole; etoposide phosphate; etoprine; fazarabine; fenretinide; floxuridine; fludarabine phosphate; fluorouracil; flurocitabine; fosquidone; fostriecin sodium; gemcitabine hydrochloride; hydroxyurea; idarubicin hydrochloride; irinotecan hydrochloride; lanreotide acetate; letrozole; leuprolide acetate; lometrexol sodium; losoxantrone hydrochloride; masoprocol; maytansine; mecchlorethamine hydrochloride; melphalan; menogaril; methotrexate sodium; metoprine; mitocarcin; mitocromin; mitogillin; mitomycin; mitoxantrone hydrochloride; mycophenolic acid; nogalamycin; ormaplatin; oxisuran; pegaspargase; peliomycin; pentamustine; peplomycin sulfate; perfosfarnide; pipobroman; piposulfan; piroxantrone hydrochloride; plicamycin; porfimer sodium; porfiromycin; prednimustine; procarbazine hydrochloride; puromycin; puromycin hydrochloride; pyrazofurin; riboprine; rogletimide; safingol; safingol hydrochloride; semustine; sparfosate sodium; sparsornycin; spirogermanium hydrochloride; spiromustine; spiroplatin; streptonigrin; streptozocin; teloxantrone hydrochloride; temoporfin; teroxirone; thiamiprine; thioguanine; tiazofurin; tirapazamine; toremifene citrate; triciribine phosphate; trimetrexate; trimetrexate glucuronate; triptorelin; tubulozole hydrochloride; uracit mustard; vapreotide; verteporfln; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozolc; zeniplatin; zinostatin; zorubicin hydrochloride, 20-epi-1,25-dihydroxyvitamin D3; abiraterone; aclarubicin; acylfulvene; adecypenol; adozelesin; aldesleukin; ALL TK antagonists; altretamine; ambamustine; amidox; arnifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein 1; antiandrogen; antiestrogen; antineoplaston; antisense oligonucleotides; aphidicolin glycinate; apoptosis regulators; apurinic acid; ara CDP DL PTBA; axinastatin 3; azatoxin; azatyrosine; baccatin III derivatives; balanol; batimastat; beta lactam derivatives; beta alethine; betaclarnycin B; betulinic acid; bFGF inhibitor; bicalutamide; bisantrene; bisaziridinylspermine; bisnafide; bistratene A; bizelesin; breflate; bropirimine; buthionine sulfoximine; calcipotriol; calphostin C; canarypox IL-2; carboxamide amino triazole; carboxyarnidotriazole; CaRest M3; CARN 700; carzelesin; castanospermine; cetrorelix; chlorins; cicaprost; cladribine; clomifene analogues; clotrimazole; combretastatin A4; conagenin; crambescidin 816; crisnatol; cyclopentanthraquinones; cytarabine ocfosfate; cytostatin; dacliximab; decitabine; deslorelin; dexamethasone; diaziquone; didemnin B; didox; diethylnorspermine; dihydro 5, azacytidine; dihydrotaxol, 9; dioxamycin; docetaxel; docosanol; doxifluridine; duocarmycin SA; ecomustine; eflomithine; elemene; emitefur; epirubicin; episteride; estramustine analogue; estrogen agonists; estrogen antagonists; etanidazole; etoposide phosphate; fazarabine; fenretinide; finasteride; flavopiridol; fltidarabine; fluorodaunoruniein hydrochloride; forfenimex; formestane; fostriecin; galocitabine; ganirelix; hexamethylene bisacetamide; hypericin; ibandronic acid; idarubicin; idramantone; ilmofosine; ilomastat; imidazoacridones; imiquimod; iobenguane; iododoxorubiein; ipomeanol, 4; irsogladine; isobengazole; itasetron; jasplakinolide; kahalalide F; larnellarin N triacetate; lanreotide; leinamycin; leptolstatin; leuprolide+estrogen+progesterone; leuprorelin; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; matrilysin inhibitors; matrix metalloproteinase inhibitors; menogaril; merbarone; meterelin; metoclopramide; MIF inhibitor; mifepristone; mirimostim; mitoguazone; mitolactol; mitomycin analogues; mitonafide; mitotoxin fibroblast growth factor saporin; mitoxantrone; monophosphoryl lipid A+myobacterium cell wall sk; mopidamol; mustard anti-cancer agent; mycaperoxide B; mycobacterial cell wall extract; myriaporone; N acetyldinaline; nafarelin; naloxone+pentazocine; napavin; naphterpin; nemorubicin; neridronic acid; nisamycin; nitrullyn; octreotide; okicenone; oligonucleotides; onapristone; oracin; osaterone; oxaunomycin; paclitaxel; paclitaxel analogues; paclitaxel derivatives; palauamine; pamidronic acid; panaxytriol; panomifene; parabactin; pazelliptine; pegaspargase; peldesine; pentosan polysulfate sodium; pentostatin; perfosfamide; perillyl alcohol; phenylacetate; phosphatase inhibitors; picibanil; pirarubicin; piritrexim; placetin A; placetin B; plasminogen activator inhibitor; platinum triamine complex; porfimer sodium; porfiromycin; prednisone; propyl his acridone; prostaglandin J2; purpurins; pyrazoloaeridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; RH retinamide; rogletimide; rohitukine; romurtide; roquinimex; rubiginone BI; ruboxyl; safingol; saintopin; SarCNU; sarcophytol A; Sdi 1, mimetics; semustine; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; sulfinosine; suradista; suramin; swainsonine; tallimustine; tauromustine; tazarotene; temoporfin; temozolomide; teniposide; tetrazomine; thiocoraline; tin ethyl etiopurpurin; tirapazamine; topsentin; toremifene; tretinoin; triciribine; trimetrexate; turosteride; ubenimex; vapreotide; variolin B; velaresol; veramine; verteporfin; vinorelbine; vinxaltine; zanoterone; zeniplatin; zilascorb; and zinostatin stimalamer.

15. A method of treating a tumor comprising administering to an individual in need thereof a therapeutically effective amount of a porphyrazine-chemotherapeutic agent conjugate of claim 14.

16. The method of claim 15 wherein the chemotherapeutic agent is doxorubicin, methotrexate, tamoxifen, taxotere, or xeloda.

17. The method of claim 15 wherein the porphyrazine is

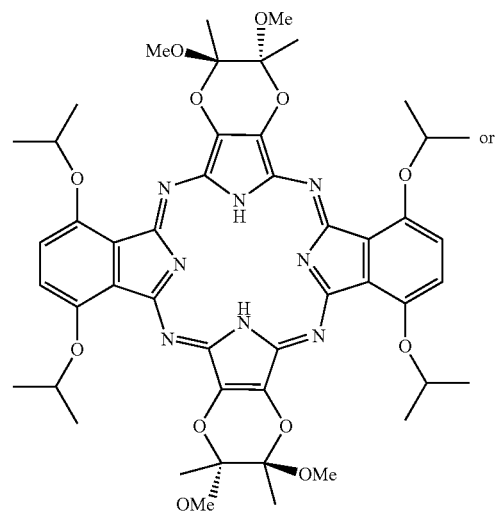

18. The method of claim 17 wherein the chemotherapeutic agent is doxorubicin, methotrexate, tamoxifen, taxotere, or xeloda.

19. The porphyrazine-chemotherapeutic agent conjugate of claim 14 wherein the porphyrazine is

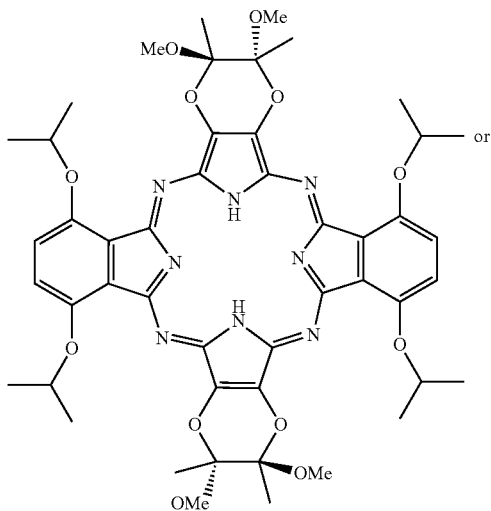

or

-continued

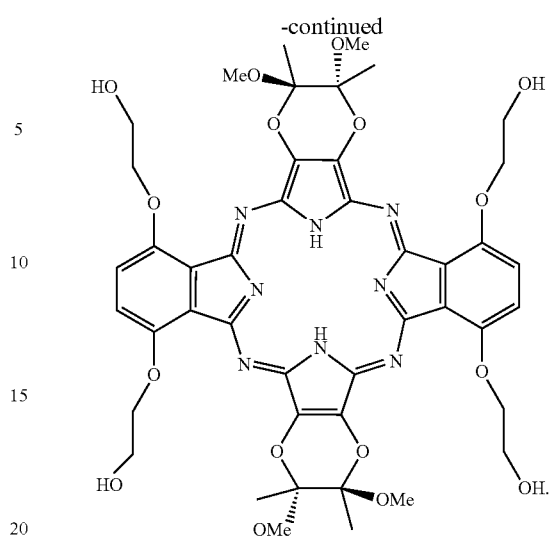

20. The porphyrazine-chemotherapeutic agent conjugate of claim 19 wherein the chemotherapeutic agent is doxorubicin, methotrexate, tamoxifen, taxotere, or xeloda.

21. The porphyrazine-chemotherapeutic agent conjugate of claim 14 wherein the chemotherapeutic agent is doxorubicin, methotrexate, tamoxifen, taxotere, or xeloda.

* * * * *